United States Patent
Mahmoudi

(10) Patent No.: US 12,262,943 B2
(45) Date of Patent: Apr. 1, 2025

(54) EXPANDABLE ABLATION MECHANISMS FOR SHUNTING CATHETERS

(71) Applicant: THERAHEART INC., Irvine, CA (US)

(72) Inventor: Rani Abdullah Mahmoudi, Huntington Beach, CA (US)

(73) Assignee: Theraheart Inc., Irvine, CA (US)

( * ) Notice: Subject to any disclaimer, the term of this patent is extended or adjusted under 35 U.S.C. 154(b) by 0 days.

(21) Appl. No.: 18/623,954

(22) Filed: Apr. 1, 2024

(65) Prior Publication Data

US 2024/0415568 A1    Dec. 19, 2024

Related U.S. Application Data

(60) Provisional application No. 63/521,187, filed on Jun. 15, 2023.

(51) Int. Cl.
A61B 18/14 (2006.01)
A61B 18/00 (2006.01)

(52) U.S. Cl.
CPC ............ *A61B 18/1492* (2013.01); *A61B 2018/00214* (2013.01); *A61B 2018/00386* (2013.01); *A61B 2018/00577* (2013.01)

(58) Field of Classification Search
CPC ................................. A61B 18/1492
See application file for complete search history.

(56) References Cited

U.S. PATENT DOCUMENTS

| | | |
|---|---|---|
| 4,861,336 A | 8/1989 | Helzel |
| 5,255,679 A | 10/1993 | Imran |
| 5,328,472 A | 7/1994 | Rupp et al. |
| 5,800,450 A | 9/1998 | Lary et al. |
| 6,179,832 B1 | 1/2001 | Tartaglia et al. |
| 6,726,677 B1 | 4/2004 | Flaherty et al. |
| 7,018,400 B2 | 3/2006 | Haarstad et al. |
| 7,150,745 B2 | 12/2006 | Stern et al. |
| 7,655,005 B2 | 2/2010 | Bhola |
| 7,674,256 B2 | 3/2010 | Marrouche et al. |
| 7,966,057 B2 | 6/2011 | Macaulay et al. |
| 8,021,359 B2 | 9/2011 | Auth et al. |
| 8,043,360 B2 | 10/2011 | McNamara et al. |

(Continued)

FOREIGN PATENT DOCUMENTS

| | | |
|---|---|---|
| CA | 2472701 C | 11/2012 |
| CN | 109965974 A | 7/2019 |

(Continued)

OTHER PUBLICATIONS

Babaliaros et al., "Emerging Applications for Transseptal Left Heart Catheterization: Old Techniques for New Procedures," J. Am. Coll.. Cardiol., 2008; 51:2116-22.

(Continued)

*Primary Examiner* — Mallika D Fairchild
*Assistant Examiner* — Thien Jason Tran
(74) *Attorney, Agent, or Firm* — Faegre Drinker Biddle & Reath LLP

(57) ABSTRACT

Some embodiments of the present disclosure are directed to systems, apparatus, and methods for creating a shunt in a patient. In some embodiments, a shunting catheter includes a puncture element and an expandable ablation mechanism for creating the shunt in the patient.

29 Claims, 24 Drawing Sheets

(56) References Cited

U.S. PATENT DOCUMENTS

| | | |
|---|---|---|
| 8,157,860 B2 | 4/2012 | McNamara et al. |
| 8,172,896 B2 | 5/2012 | McNamara et al. |
| 8,214,015 B2 | 7/2012 | Macaulay et al. |
| 8,226,619 B2 | 7/2012 | Smith et al. |
| 8,252,042 B2 | 8/2012 | McNamara et al. |
| 8,374,680 B2 | 2/2013 | Thompson |
| 8,585,596 B1 | 11/2013 | Flaherty et al. |
| 8,617,152 B2 | 12/2013 | Flaherty et al. |
| 8,728,073 B2 | 5/2014 | McDaniel |
| 8,758,363 B2 | 6/2014 | Nishtala et al. |
| 8,874,237 B2 | 10/2014 | Schilling |
| 8,882,697 B2 | 11/2014 | McNamara et al. |
| 8,900,250 B2 | 12/2014 | Fritscher-Ravens et al. |
| 8,926,602 B2 | 1/2015 | Pageard |
| 8,968,233 B2 | 3/2015 | Duffy et al. |
| 9,089,314 B2 | 7/2015 | Wittenberger |
| 9,345,858 B2 | 5/2016 | Flaherty et al. |
| 9,468,744 B2 | 10/2016 | Arana et al. |
| 9,642,993 B2 | 5/2017 | McNamara et al. |
| 9,789,294 B2 | 10/2017 | Taft et al. |
| 9,808,303 B2 | 11/2017 | Gelfand et al. |
| 9,808,304 B2 | 11/2017 | Lalonde |
| 9,814,483 B2 | 11/2017 | Vardi |
| 9,918,789 B2 | 3/2018 | Bagley et al. |
| 10,016,620 B2 | 7/2018 | Aljuri et al. |
| 10,039,905 B1 | 8/2018 | Taft et al. |
| 10,154,878 B2 | 12/2018 | Greenlaw et al. |
| 10,188,375 B2 | 1/2019 | McNamara et al. |
| 10,207,126 B2 | 2/2019 | Benson |
| 10,245,352 B2 | 4/2019 | Wilson et al. |
| 10,327,791 B2 | 6/2019 | Argentine et al. |
| 10,426,497 B2 | 10/2019 | Chou et al. |
| 10,449,339 B2 | 10/2019 | Wilson et al. |
| 10,568,688 B2 | 2/2020 | Hu et al. |
| 10,568,751 B2 | 2/2020 | McNamara |
| 10,624,621 B2 | 4/2020 | Celermajer |
| 10,639,060 B2 | 5/2020 | Vardi et al. |
| 10,722,300 B2 | 7/2020 | Gupta et al. |
| 10,729,492 B2 | 8/2020 | Brown et al. |
| 10,758,714 B2 | 9/2020 | Laby et al. |
| 10,842,562 B2 | 11/2020 | Zhang et al. |
| 10,857,328 B2 | 12/2020 | Walzman |
| 10,864,041 B2 | 12/2020 | Urbanski et al. |
| 10,932,723 B2 | 3/2021 | Eliason et al. |
| 10,980,552 B2 | 4/2021 | Mustapha |
| 10,987,494 B2 | 4/2021 | Skinner et al. |
| 10,993,735 B2 | 5/2021 | Vardi et al. |
| 10,993,736 B2 | 5/2021 | Vardi et al. |
| 11,052,246 B2 | 7/2021 | Stewart et al. |
| 11,065,019 B1 | 7/2021 | Chou et al. |
| 11,071,585 B2 | 7/2021 | Zhang et al. |
| 11,083,520 B2 | 8/2021 | Ghaly et al. |
| 11,135,410 B2 | 10/2021 | Finch et al. |
| 11,224,449 B2 | 1/2022 | Chou et al. |
| 11,224,450 B2 | 1/2022 | Chou et al. |
| 11,350,990 B2 | 6/2022 | Gupta et al. |
| 11,369,346 B2 | 6/2022 | Stigall et al. |
| 11,369,405 B2 | 6/2022 | Vardi et al. |
| 11,399,852 B2 | 8/2022 | Wilson et al. |
| 11,534,239 B2 | 12/2022 | Bishara et al. |
| 11,612,432 B2 | 3/2023 | Pate et al. |
| 11,648,042 B2 | 5/2023 | Kelley |
| 11,690,609 B2 | 7/2023 | Celermajer |
| 11,717,429 B2 | 8/2023 | Schwartz et al. |
| 11,752,314 B2 | 9/2023 | Taft et al. |
| 11,793,529 B2 | 10/2023 | Chou et al. |
| 11,806,032 B2 | 11/2023 | Chou et al. |
| 11,865,282 B2 | 1/2024 | Nae et al. |
| 11,957,374 B2 | 4/2024 | Vardi et al. |
| 12,004,802 B2 | 6/2024 | Scott et al. |
| 2005/0154386 A1* | 7/2005 | West ............... A61B 18/1492 |
| | | 606/41 |
| 2005/0171527 A1 | 8/2005 | Bhola |
| 2006/0135961 A1 | 6/2006 | Rosenman et al. |
| 2007/0083194 A1 | 4/2007 | Kunis et al. |
| 2009/0125097 A1 | 5/2009 | Bruszewski et al. |
| 2012/0123466 A1 | 5/2012 | Porter et al. |
| 2012/0130417 A1 | 5/2012 | Lepulu et al. |
| 2014/0277054 A1 | 9/2014 | McNamara et al. |
| 2015/0209526 A1 | 7/2015 | Matsubara et al. |
| 2016/0175041 A1 | 6/2016 | Govari et al. |
| 2018/0236211 A1 | 8/2018 | Henschel |
| 2019/0374254 A1 | 12/2019 | Arevalos et al. |
| 2020/0030588 A1 | 1/2020 | Heilman et al. |
| 2020/0038672 A1 | 2/2020 | Satake |
| 2020/0170662 A1* | 6/2020 | Vardi ............... A61B 17/3205 |
| 2020/0238059 A1* | 7/2020 | Wang ............... A61M 27/002 |
| 2020/0261704 A1 | 8/2020 | Wang et al. |
| 2020/0367924 A1 | 11/2020 | Lenker et al. |
| 2021/0038298 A1 | 2/2021 | Scott et al. |
| 2021/0045805 A1 | 2/2021 | Govari et al. |
| 2021/0085384 A1 | 3/2021 | Morey et al. |
| 2021/0196373 A1 | 7/2021 | He et al. |
| 2021/0228227 A1 | 7/2021 | Vardi et al. |
| 2021/0315629 A1 | 10/2021 | Yang et al. |
| 2021/0369321 A1 | 12/2021 | Yang et al. |
| 2021/0393324 A1 | 12/2021 | Moriyama et al. |
| 2022/0022954 A1 | 1/2022 | Shuros et al. |
| 2022/0110679 A1 | 4/2022 | Wang et al. |
| 2022/0249160 A1 | 8/2022 | Pate et al. |
| 2022/0257318 A1* | 8/2022 | Belalcazar ......... A61B 18/1206 |
| 2022/0265346 A1 | 8/2022 | Gupta et al. |
| 2022/0273279 A1 | 9/2022 | Valdez et al. |
| 2022/0330975 A1* | 10/2022 | Rafiee ............... A61M 25/0082 |
| 2023/0041021 A1 | 2/2023 | Urbanski et al. |
| 2023/0078647 A1 | 3/2023 | Sharma et al. |
| 2023/0099410 A1 | 3/2023 | Primeaux |
| 2023/0210592 A1 | 7/2023 | Agnew et al. |
| 2023/0248425 A1 | 8/2023 | Tijima |
| 2023/0270491 A1 | 8/2023 | Mori et al. |
| 2023/0293877 A1 | 9/2023 | Hoem |
| 2024/0050717 A1 | 2/2024 | Rickerson et al. |

FOREIGN PATENT DOCUMENTS

| | | |
|---|---|---|
| CN | 115475001 A | 12/2022 |
| CN | 115590605 A | 1/2023 |
| EP | 1878453 B1 | 12/2014 |
| EP | 3238646 A2 | 11/2017 |
| EP | 3705154 A1 | 9/2020 |
| JP | 5237572 B2 | 7/2013 |
| WO | 2003/049643 A1 | 6/2003 |
| WO | 2018/229768 A2 | 12/2018 |
| WO | 2018/229768 A9 | 12/2018 |
| WO | 2020/024612 A1 | 2/2020 |
| WO | 2020/232384 A1 | 11/2020 |
| WO | 2020/242491 A1 | 12/2020 |
| WO | 2021/091566 A1 | 5/2021 |
| WO | 2021/190547 A1 | 9/2021 |
| WO | 2022/113054 A1 | 6/2022 |
| WO | 2022/135375 A1 | 6/2022 |
| WO | 2022/166973 A1 | 8/2022 |
| WO | 2022/246158 A1 | 11/2022 |
| WO | 2023/088572 A1 | 5/2023 |

OTHER PUBLICATIONS

Edwards Lifesciences, "The Alt-Flow II trial for heart failure," 10 pages (undated).

Tanaka et al., "Treatment of Hepatic Encephalopathy Due to Inferior Mesenteric Vein/Inferior Vena Cava and Gonadal Vein Shunt Using Dual Balloon-Occluded Retrograde Transvenous Obliteration," Cardiovasc Intervent Radiol, 2009, 32:390-393 (published online Oct. 7, 2008).

United States Patent and Trademark Office, Office Action mailed May 17, 2024, for U.S. Appl. No. 18/624,014.

Wilson et al., "Successful Tanscatheter Occlusion of an Anomalous Pulmonary Vein With Dual Drainage to the Left Atrium," Catheter Cardiovasc Interv, 2015, 85:1212-1216 (published online in Wiley Online Library, Apr. 7, 2015).

Patent Cooperative Treaty, International Search Report, mailed Jul. 17, 2024, in PCT/US2024/022547.

(56) References Cited

OTHER PUBLICATIONS

Patent Cooperative Treaty, International Search Report, mailed Jul. 25, 2024, in PCT/US2024/023345.
Patent Cooperative Treaty, International Search Report, mailed Jun. 24, 2024, in PCT/US2024/018244.
Patent Cooperative Treaty, Written Opinion, mailed Jul. 17, 2024, in PCT/US2024/022547.
Patent Cooperative Treaty, Written Opinion, mailed Jul. 25, 2024, in PCT/US2024/023345.
Patent Cooperative Treaty, Written Opinion, mailed Jun. 24, 2024, in PCT/US2024/018244.
United States Patent and Trademark Office, Office Action mailed Jul. 12, 2024, for U.S. Appl. No. 18/593,832.

* cited by examiner

EXPANDABLE ABLATION MECHANISMS FOR SHUNTING CATHETERS

CROSS-REFERENCE TO RELATED APPLICATION

The present application claims the benefit of U.S. Provisional Application No. 63/521,187, entitled "EXPANDABLE ABLATION MECHANISMS FOR SHUNTING CATHETERS," filed on Jun. 15, 2023, which is incorporated by reference herein for all purposes in its entirety.

TECHNICAL FIELD

Certain embodiments of the present disclosure relate to medical systems, apparatus, and methods for creating a shunt in a patient. More specifically, some embodiments of the present disclosure relate to medical systems, apparatus, and methods for creating a shunt on a cardiovascular system wall in a patient.

BACKGROUND

Heart failure is a serious condition that occurs when a heart cannot pump enough blood and oxygen to support other organs in the body. Heart failure is classified according to left ventricular (LV) function as "heart failure with reduced ejection fraction (EF)" (HFrEF; EF<40%), "mid-range EF" (HFmrEF; EF 40-49%), or "preserved EF" (HFpEF; EF≥50%). About half the patients with heart failure have HFpEF. HFpEF generally occurs when LV and left atrial filling pressures increase significantly during exercise, with an associated increase in pulmonary pressures leading to pulmonary congestion. Structural interventions to lower elevated either left or right atrial filling pressures are gaining attention.

Studies in heart failure show that lowering left atrial pressure may reduce cardiovascular events while improving functional capacity. The creation of an interatrial shunt has emerged as a therapy to decompress the left atrium in patients with acute and chronic left HF. As such, attention has turned toward the development of interatrial shunt devices (IASDs) as a means of reducing the detrimental increase in left-sided filling pressures with exercise in an effort to improve symptomatology. The IASDs may be used to treat various kinds of heart failure and/or other diseases that may result in too high of a pressure in the right atrium of a patient.

SUMMARY

Many IASDs reside in the interatrial septum, with risk for right-to-left shunting and systemic embolization. Moreover, preservation of the interatrial septum is important with an increasing number of left-sided transseptal transcatheter interventions. Improved IASDs for safer and better procedures are needed.

According to some embodiments of the present disclosure, a shunting catheter includes: a catheter shaft including a shaft lumen; an ablation shaft disposed in the shaft lumen at a first state and extended from the catheter shaft at a second state; and an ablation mechanism disposed on the ablation shaft and expandable at the second state, the ablation mechanism including a plurality of expandable struts; wherein the ablation mechanism is configured to receive energy from an energy source and deliver ablation energy to a target location of a patient.

According to some embodiments, a method for creating a shunt includes: deploying a shunting catheter in a first state, the shunting catheter including: a catheter shaft including a shaft lumen; an ablation shaft disposed in the shaft lumen at a first state; and an ablation mechanism disposed on the ablation shaft and including a plurality of expandable struts; disposing the shunting catheter proximate to a target location of a patient; operating the shunting catheter to a second state, wherein the ablation shaft and the ablation mechanism extend from the catheter shaft; expanding an opening at the target location of the patient by expanding the plurality of expandable struts; and delivering ablation energy via the ablation mechanism to the target location of the patient.

According to certain embodiments, a shunting catheter system includes: a shunting catheter, including: a catheter shaft including a shaft lumen; an ablation shaft disposed in the shaft lumen at a first state and extended from the catheter shaft at a second state; and an ablation mechanism disposed on the ablation shaft, the ablation mechanism including a plurality of expandable struts defining an expandable cage; an energy source connected to the shunting catheter; and a controller connected to the energy source and including a processor; wherein the processor is configured to control the energy source to deliver ablation energy to a target location of a patient via the ablation mechanism.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
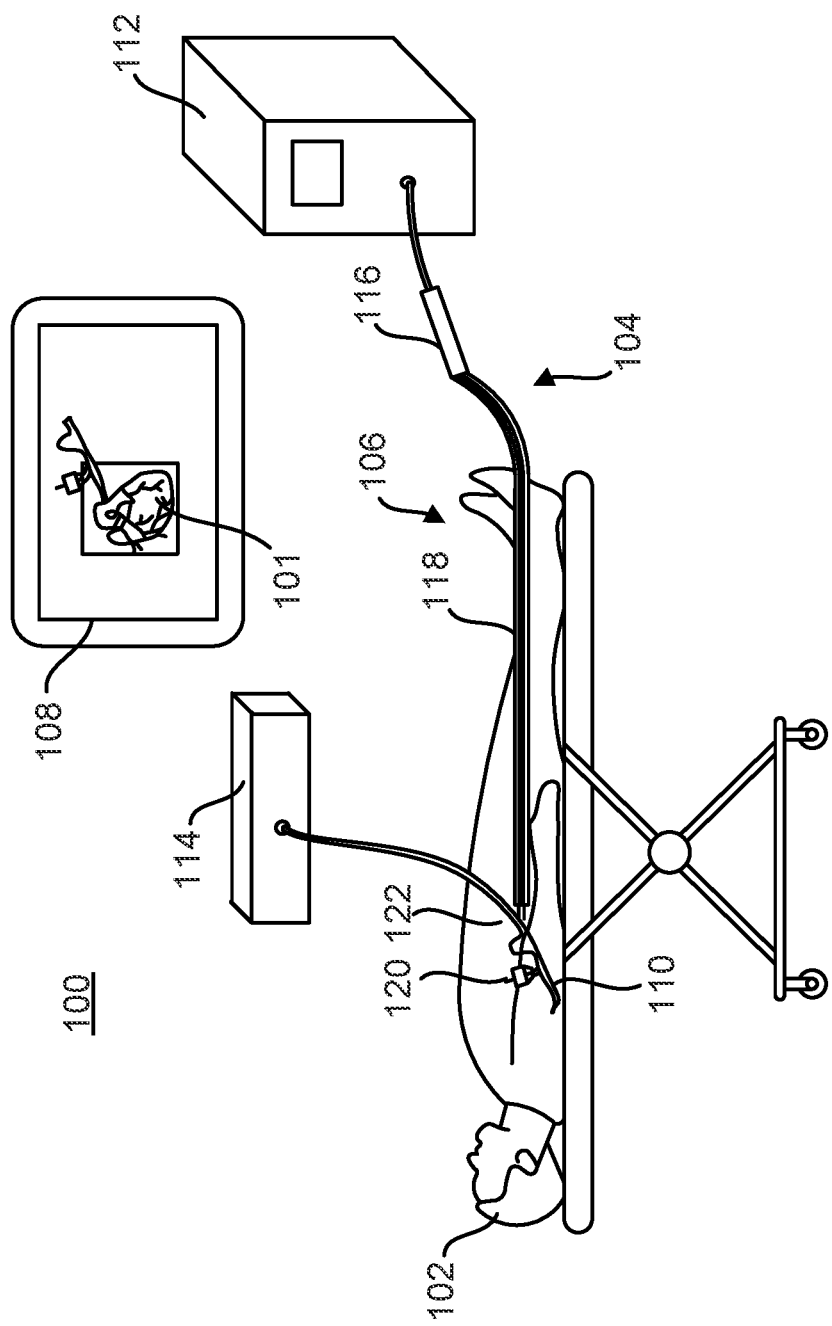
FIG. 1 is a diagram illustrating an exemplary clinical setting for treating a heart of the patient using a shunting catheter system, in accordance with embodiments of the present disclosure.

While the present disclosure is amenable to various modifications and alternative forms, specific embodiments have been shown by way of example in the drawings and are described in detail below. The present disclosure, however, is not to limit the present disclosure to the particular embodiments described. On the contrary, the present disclosure is intended to cover all modifications, equivalents, and alternatives falling within the scope of the present disclosure as defined by the appended claims.

DETAILED DESCRIPTION

The following detailed description is exemplary in nature and is not intended to limit the scope, applicability, or configuration of the present disclosure in any way. Rather, the following description provides some practical illustrations for implementing exemplary embodiments of the present disclosure. Examples of constructions, materials, and/or dimensions are provided for selected elements. Those skilled in the art will recognize that many of the noted examples have a variety of suitable alternatives.

Unless otherwise indicated, all numbers expressing feature sizes, amounts, and physical properties used in the specification and claims are to be understood as being modified in all instances by the term "about." Accordingly, unless indicated to the contrary, the numerical parameters set forth in the foregoing specification and attached claims are approximations that can vary depending upon the desired properties sought to be obtained by those skilled in the art utilizing the teachings disclosed herein. The use of numerical ranges by endpoints includes all numbers within that range (for example, 1 to 5 includes 1, 1.5, 2, 2.75, 3, 3.80, 4, and 5) and any number within that range.

Although illustrative methods may be represented by one or more drawings (for example, flow diagrams, communication flows, etc.), the drawings should not be interpreted as implying any requirement of, or particular order among or between, various steps disclosed herein. However, some embodiments may require certain steps and/or certain orders between certain steps, as may be explicitly described herein and/or as may be understood from the nature of the steps themselves (for example, the performance of some steps may depend on the outcome of a previous step). Additionally, a "set," "subset," or "group" of items (for example, inputs, algorithms, data values, etc.) may include one or more items and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information. In some embodiments, the term "receive" or "receiving" means obtaining from a data repository (for example, database), from another system or service, from another software, or from another software component in a same software. In certain embodiments, the term "access" or "accessing" means retrieving data or information, and/or generating data or information.

There are various approaches for creating an interatrial shunt, which is a connection or gateway between the left and right atria of a patient's heart for blood to flow through. In some embodiments, examples of interatrial shunt devices (IASDs) include implants or shunting catheters. For example, devices reside in the interatrial septum, with risk for right-to-left shunting and systemic embolization. In some examples, preservation of the interatrial septum is important with an increasing number of left-sided transseptal transcatheter interventions. Improved IASDs for safer and better procedures are needed. At least some embodiments of the present disclosure are directed to a shunting catheter for deployment through a patient's coronary sinus (CS) for creating a shunt between the CS and the patient's left atrium (LA). At least some embodiments of the present disclosure are directed to a shunting catheter for deployment through a patient's atrial septum (AS) for creating a shunt between the patient's right atrium (RA) and LA.

A patient's CS ostium may have a diameter of from about 10 mm to about 20 mm. As the CS is a relatively small vessel, at least some embodiments of the present disclosure include features of a shunting catheter that helps protect a patient's vessels during deployment and/or elements for stabilizing the catheter during the procedure. In embodiments, the shunting catheter includes a catheter shaft and an ablation assembly, the ablation assembly including an ablation shaft and an ablation mechanism. The shunting catheter further includes a puncture mechanism disposed proximate to a distal end of the ablation mechanism. In some embodiments, the catheter shaft is made of flexible materials that bends according to the anatomy of the CS to conform to the shape of the patient's CS. In some embodiments, the catheter shaft includes a stabilizing element such as distal tip that has a curve (for example, a pre-existing curve) conforming to the shape of a patient's CS to help stabilize the catheter and minimize potential damage to the vessel wall of a patient's CS.

In certain embodiments, the ablation assembly is disposed in a shaft lumen of the catheter shaft at a first state, and is extended from the catheter shaft at a second state. In some embodiments, a shunt is formed by creating an opening between the patient's CS and LA. In some embodiments, a shunt is formed by creating an opening between the patient's RA and LA. In certain embodiments, the shunting catheter is inserted through the patient's superior vena cava (SVC)

via a transjugular approach. In certain embodiments, the shunting catheter is inserted through the patient's inferior vena cava (IVC) via a transfemoral approach.

FIG. 1 is a diagram illustrating an exemplary clinical setting 100 for treating a heart 101 of a patient 102 using a shunting catheter system 104, in accordance with embodiments of the present disclosure. In certain embodiments, the shunting catheter system 104 includes a shunting device 106. As will be appreciated by the skilled artisan, the clinical setting 100 may have other components and arrangements of components that are not shown in FIG. 1. In some embodiments, the shunting catheter system 104 includes or is coupled to an imaging system (for example, an X-ray system), which may include one or more visualization elements and a display 108. In some embodiments, one or more visualization elements may be disposed on the shunting device 106. In certain embodiments, the imaging system can help guide a physician's operation of the shunting device 106 during a procedure.

According to certain embodiments, the shunting device 106 includes a shunting catheter 110, a controller 112, and an energy source 114 (for example, a generator). In some embodiments, the controller 112 is configured to control functional aspects of the shunting device 106. In some embodiments, the controller 112 is configured to control the energy source 114 to deliver energy to the shunting catheter 110. In certain embodiments, the controller 112 may be connected to the one or more visualization elements to facilitate positioning of the shunting catheter 110 in a patient's heart during procedure. In some embodiments, the energy source 114 is connected to the controller 112. In some embodiments, the energy source 114 may be integrated with the controller 112.

According to some embodiments, the shunting device 106 includes a handle 116, a catheter shaft 118, and an ablation assembly 120. In certain embodiments, the handle 116 is configured to be operated by a user to position the ablation assembly 120 at a target shunting location. In certain embodiments, the ablation assembly 120 includes a puncture element (for example, a puncture needle) configured to puncture through a vessel wall. In certain embodiments, the ablation assembly 120 is connected to the energy source 114 to provide shunting. For example, the ablation assembly 120 receives energy from the energy source 114 to deliver energy (for example, ablation energy, such as radiofrequency (RF) energy, phased RF energy, cryogenic energy, thermal energy, pulse energy, laser energy, microwave energy, ultrasound energy, and/or the like) to the target location (for example, a target tissue) at a cardiovascular system (for example, a circulatory system) wall. In certain embodiments, the energy source 114 provides energy in a first form (for example, electrical energy) to the ablation assembly 120, and the ablation assembly 120 delivers the ablation energy to the target location in a second form (for example, radiofrequency (RF) energy, phased RF energy, cryogenic energy, thermal energy, pulse energy, laser energy, microwave energy, ultrasound energy, and/or the like).

According to certain embodiments, during deployment, the shunting device 106 including a portion of the catheter shaft 118 enters through a patient's CS ostium. The shunting device 106 may then be oriented through one or more mechanisms in the patient's CS, as will be discussed in more detail below. In some embodiments, in order to conform to the shape of the patient's CS, the catheter shaft 118 is made of flexible materials and/or has a structure that may bend according to the anatomy of the CS. In certain embodiments, during deployment, the puncture element creates an opening at a target tissue (for example, a vessel wall), and then the ablation assembly 120 enlarges the opening at the target tissue.

In certain embodiments, the controller 112 controls the delivery of ablation energy (for example, radiofrequency (RF) energy, phased RF energy, cryogenic energy, thermal energy, pulse energy, laser energy, microwave energy, ultrasound energy, and/or the like) via the ablation assembly 120 after and/or when the opening is generated by the puncture element and/or the ablation assembly 120.

In certain embodiments, the shunting catheter 110 includes a cage having a plurality of expandable struts. In certain embodiments, the struts are configured to receive energy from the energy source and deliver ablation energy to a target location of a patient. In certain embodiments, one or more of the struts carry an electrode, and the electrode is configured to receive energy from the energy source and deliver ablation energy to a target location of a patient. In certain embodiments, the struts comprise braided wires. In certain embodiments, the ablation mechanism comprises a laser-cut tube, and the struts are disposed at an end of the laser-cut tube. In some embodiments, the struts are self-expandable. In certain embodiments, the struts are expandable via an actuator (for example, an inflatable balloon) carried within the cage. In certain embodiments, the struts are constructed of at least one material selected from a group consisting of nitinol, stainless steel, titanium, platinum-iridium, and cobalt-chromium.

In certain embodiments, the shunting catheter 110 includes an apposition element 122 disposed proximate to the ablation assembly 120. In some embodiments, the apposition element 122 is disposed within a shaft (for example, an outer shaft) at the first state. In some embodiments, the apposition element 122 is protruded from the catheter shaft 118 at the first state and/or at the second state. In certain embodiments, the apposition element 122 can appose to a cardiovascular system wall (for example, the front wall or back wall of the CS, a left atrium wall, a right atrium wall, etc.) at the second state, for example, to help position and/or stabilize the ablation assembly 120. In certain embodiments, the apposition element 122 includes a braid structure. In some embodiments, the apposition element 122 may include a nitinol braid that can be held within the catheter shaft 118. In certain embodiments, after deployment and stabilization of the catheter shaft 118, the ablation assembly 120 and the puncture element may then be deployed. In some embodiments, the ablation assembly 120 is configured to deliver ablation energy to target tissues for creating a shunt in the patient's CS or AS.

According to some embodiments, various components (for example, the controller 112) of the shunting catheter system 104 may be implemented on one or more computing devices. In certain embodiments, a computing device may include any type of computing device suitable for implementing embodiments of the disclosure. Examples of computing devices include specialized computing devices or general-purpose computing devices such as workstations, servers, laptops, portable devices, desktop, tablet computers, hand-held devices, general-purpose graphics processing units (GPGPUs), and the like, all of which are contemplated within the scope of FIG. 1 with reference to various components of the shunting catheter system 104.

In some embodiments, a computing device (for example, the controller 112) includes a bus that, directly and/or indirectly, couples the following devices: a processor, a memory, an input/output (I/O) port, an I/O component, and a power supply. Any number of additional components, different components, and/or combinations of components may also be included in the computing device. The bus represents what may be one or more busses (such as, for example, an address bus, data bus, or combination thereof). Similarly, in some embodiments, the computing device may include a number of processors, a number of memory components, a number of I/O ports, a number of I/O components, and/or a number of power supplies. Additionally, any number of these components, or combinations thereof, may be distributed and/or duplicated across a number of computing devices. In some embodiments, various components or parts of components (for example, controller 112, shunting catheter 110, etc.) can be integrated into a physical device.

In some embodiments, the shunting catheter system 104 includes one or more memories (not illustrated). The one or more memories includes computer-readable media in the form of volatile and/or nonvolatile memory, transitory and/or non-transitory storage media and may be removable, nonremovable, or a combination thereof. Media examples include Random Access Memory (RAM); Read Only Memory (ROM); Electronically Erasable Programmable Read Only Memory (EEPROM); flash memory; optical or holographic media; magnetic cassettes, magnetic tape, magnetic disk storage or other magnetic storage devices; data transmissions; and/or any other medium that can be used to store information and can be accessed by a computing device such as, for example, quantum state memory, and/or the like. In some embodiments, the one or more memories store computer-executable instructions for causing a processor (for example, the controller 112) to implement aspects of embodiments of system components discussed herein and/or to perform aspects of embodiments of methods and procedures discussed herein.

Computer-executable instructions may include, for example, computer code, machine-useable instructions, and the like such as, for example, program components capable of being executed by one or more processors associated with a computing device. Program components may be programmed using any number of different programming environments, including various languages, development kits, frameworks, and/or the like. Some or all of the functionality contemplated herein may also, or alternatively, be implemented in hardware and/or firmware.

In some embodiments, the memory may include a data repository that may be implemented using any one of the configurations described below. A data repository may include random access memories, flat files, XML files, and/or one or more database management systems (DBMS) executing on one or more database servers or a data center. A database management system may be a relational DBMS (RDBMS), hierarchical DBMS (HDBMS), multidimensional DBMS (MDBMS), object oriented DBMS (ODBMS or OODBMS) or object relational DBMS (ORDBMS), and/or the like. The data repository may be, for example, a single relational database. In some cases, the data repository may include a plurality of databases that can exchange and aggregate data by a data integration process or software application. In an exemplary embodiment, at least part of the data repository may be hosted in a cloud data center. In some cases, a data repository may be hosted on a single computer, a server, a storage device, a cloud server, or the like. In some other cases, a data repository may be hosted on a series of networked computers, servers, or devices. In some cases, a data repository may be hosted on tiers of data storage devices including local, regional, and central.

Various components of the shunting catheter system 104 can communicate via or be coupled to via a communication interface, for example, a wired or wireless interface. The communication interface includes, but is not limited to, any wired or wireless short-range and long-range communication interfaces. The wired interface can use cables, umbilicals, and the like. The short-range communication interfaces may be, for example, local area network (LAN), interfaces conforming to known communications standards, such as Bluetooth™ standard, IEEE 802 standards (for example, IEEE 802.11), a ZigBee™ or similar specification, such as those based on the IEEE 802.15.4 standard, or other public or proprietary wireless protocol. The long-range communication interfaces may be, for example, wide area network (WAN), cellular network interfaces, satellite communication interfaces, etc. The communication interface may be either within a private computer network, such as intranet, or on a public computer network, such as the internet. Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

Figure 2:
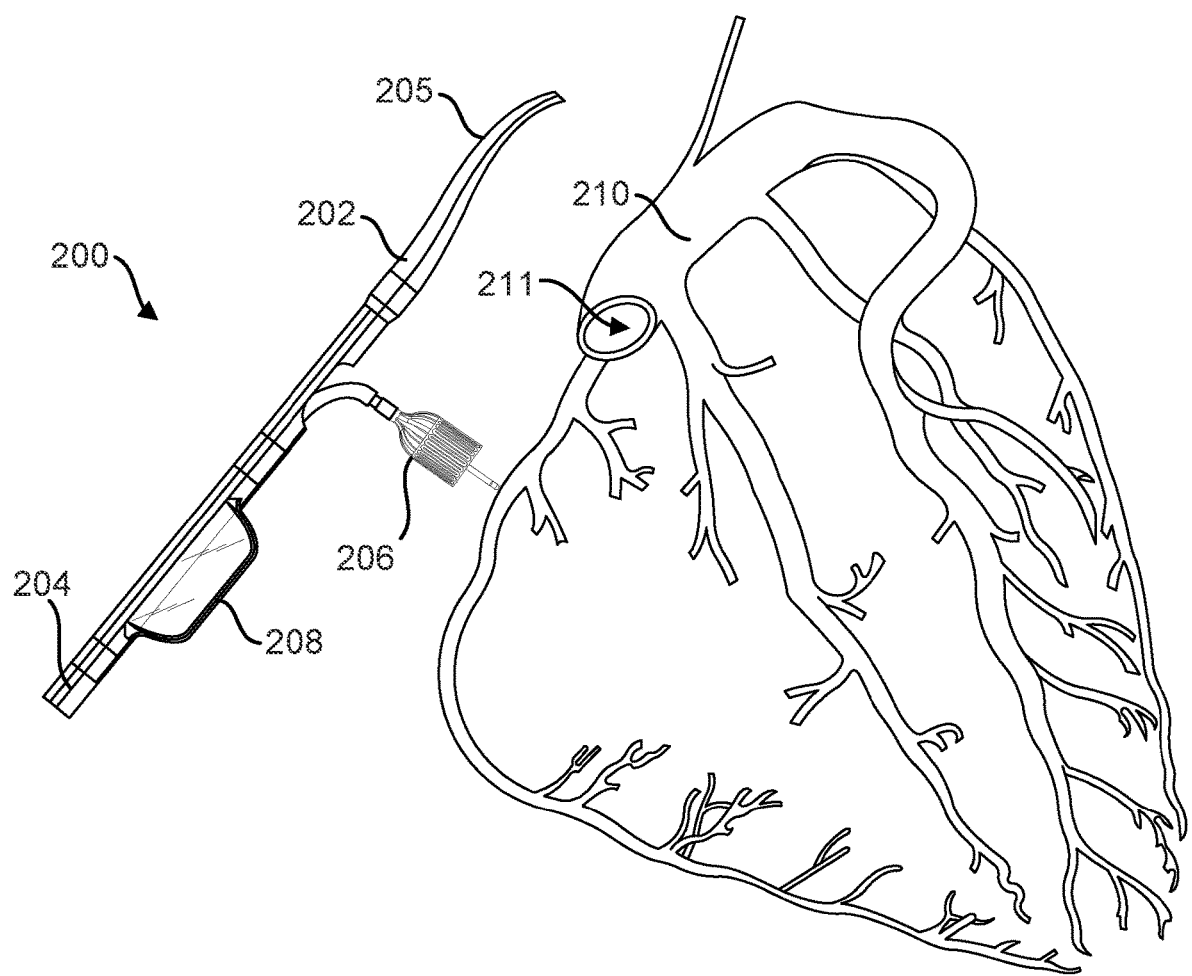
FIG. 2 is a schematic diagram illustrating an example of a shunting catheter to be deployed in a heart of a patient, in accordance with embodiments of the present disclosure.

FIG. 2 is a schematic diagram illustrating an example of a shunting device 200 to be deployed in a heart of a patient, in accordance with embodiments of the present disclosure. FIG. 2 is merely an example. One of the ordinary skilled in the art would recognize many variations, alternatives, and modifications. As shown, the shunting device 200 includes a shunting catheter 202 to be deployed to a patient's coronary sinus (CS) 210 via the CS ostium 211. In certain embodiments, the shunting catheter 202 is deployed to a patients right atrium (RA) via the inferior vena cava (IVC). In some embodiments, the shunting catheter 202 includes a catheter shaft 204, an ablation assembly 206, and an apposition element 208. In certain embodiments, the catheter shaft 204 has a curve at its distal end 205. In some embodiments, as illustrated, the ablation assembly 206 is extended from the catheter shaft 204 at a state to provide shunting (for example, a second state different from a first state to deploy the catheter 202). In certain examples, the ablation assembly 206 forms an angle greater than 10 degrees from the distal end 205 of the catheter shaft 204. In some examples, the ablation assembly 206 forms an angle greater than 30 degrees from the distal end 205 of the catheter shaft 204. In some embodiments, the ablation assembly 206 forms an angle proximate to 90 degrees from the catheter shaft 204. In some embodiments, the ablation assembly 206 forms an angle in the range of 10 degrees to 120 degrees from the catheter shaft 204.

In some embodiments, the ablation assembly 206 includes a cage having a plurality of expandable struts. In certain embodiments, the struts are configured to receive energy from the energy source and deliver ablation energy to a target location of a patient. In certain embodiments, one or more of the struts carry an electrode, and the electrode is configured to receive energy from the energy source and deliver ablation energy to a target location of a patient. In certain embodiments, the struts comprise braided wires. In certain embodiments, the ablation mechanism comprises a laser-cut tube, and the struts are disposed at an end of the laser-cut tube. In some embodiments, the struts are self-expandable. In certain embodiments, the struts are expandable via an actuator (for example, an inflatable balloon) carried within the cage. In certain embodiments, the struts are constructed of at least one material selected from a group consisting of nitinol, stainless steel, titanium, platinum-iridium, and cobalt-chromium.

In some embodiments, the catheter shaft 204 is made of flexible material that may curve with the anatomy of the patient's CS 210. In certain embodiments, for example, the catheter shaft 204 may include polyether block amide, nylon, silicone, or a combination thereof. In some embodiments, the catheter shaft 204 may be a multi-layered and multi-material component. In some examples, the catheter shaft 204 is reinforced with a braid and/or can have an etched or casted liner. In certain embodiments, the braid for reinforcing the catheter shaft 204 may be made of nitinol. In some embodiments, the liner may be made from polyetheretherketone (PEEK), polytetrafluoroethylene (PTFE), copolymers of polyamide and polyether, or a combination thereof. In some embodiments, the catheter shaft 204 is coated for lubricity with a hydrophilic coating, or other types of coating suitable for coating a catheter shaft as known by a skilled person in the art.

In some embodiments, the shunting catheter 202 has a diameter of from about 2 mm to about 5 mm. In certain embodiments, the shunting catheter 202 has a diameter from about 2.5 mm to about 4.5 mm. In some embodiments, the shunting catheter 202 has a diameter from about 3 mm to about 4 mm. In certain embodiments, the shunting catheter 202 may have a diameter allowing it to pass through vessels and parts of the cardiovascular system to reach a target location.

Figure 3:
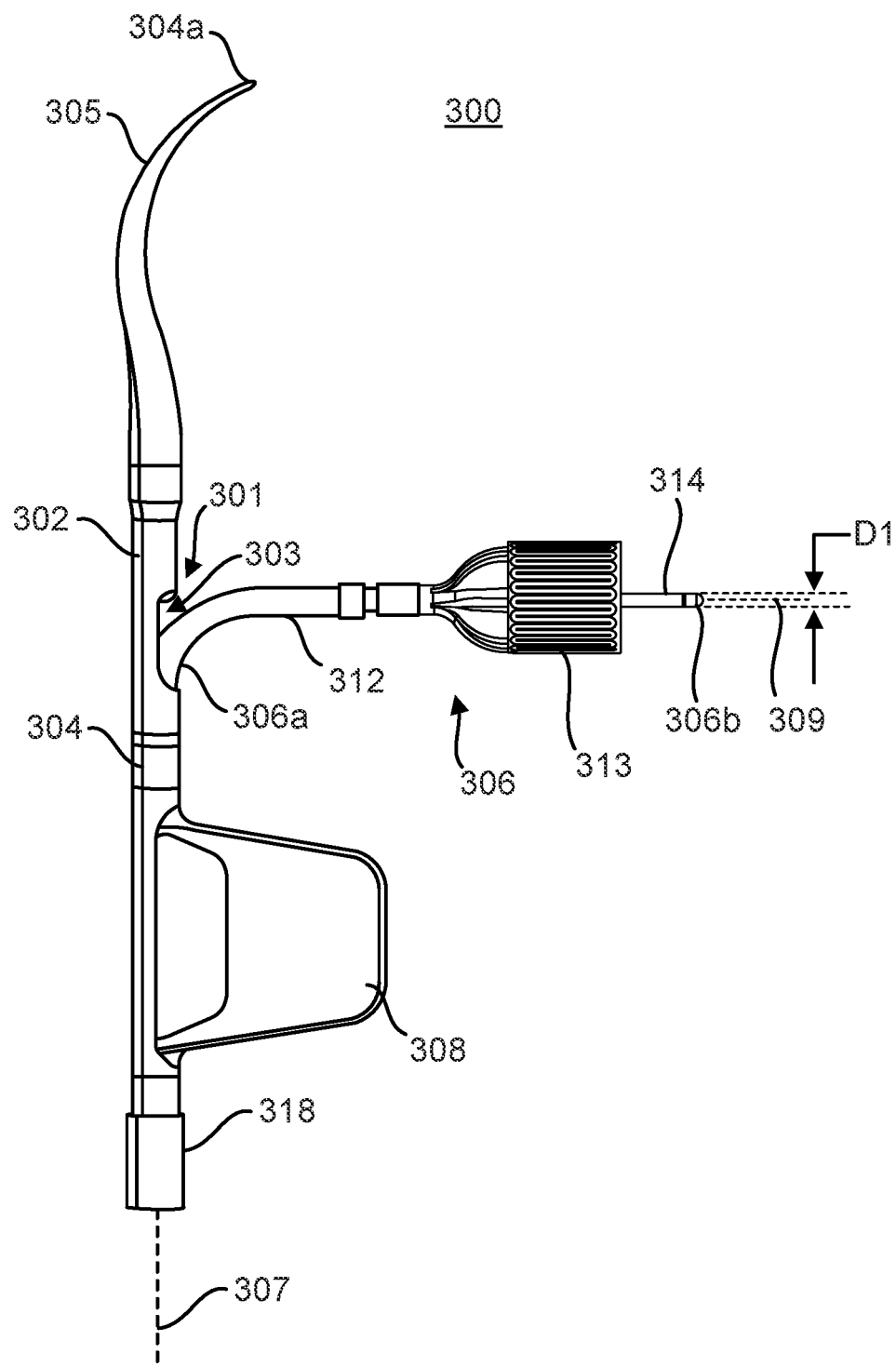
FIG. 3 is a schematic diagram of a side view of an example of a shunting catheter, in accordance with embodiments of the present disclosure.

FIG. 3 is a schematic diagram of a side view of an example of a shunting device 300, in accordance with embodiments of the present disclosure. FIG. 3 is merely an example. One of the ordinary skilled in the art would recognize many variations, alternatives, and modifications. As shown, the shunting device 300 includes a shunting catheter 302. In some embodiments, the shunting catheter is configured to be delivered through a patient's coronary sinus (CS). In some embodiments, the shunting catheter 302 includes a catheter shaft 304, an ablation assembly 306, and an apposition element 308.

According to some embodiments, the shunting catheter 302 may be inserted through a small vein in the patient's body, and then tracked to the patient's right atrium (RA). In certain embodiments, once the shunting catheter 302 is in the patient's RA, the shunting catheter 302 may be maneuvered into the CS ostium to gain alignment in the CS at a target location of on a wall between the patient's CS and LA. In other embodiments, once the shunting catheter 302 is in the patient's RA, the shunting catheter 302 may be aligned at a target location of the patient's atrial septum (AS).

According to certain embodiments, the catheter shaft 304 is made of flexible material that may curve with the anatomy of the patient's CS. In certain embodiments, the catheter shaft 304 may include polyether block amide, nylon, silicone, and/or a combination thereof. In some instances, the catheter shaft 304 may be a multi-layered and multi-material component. In some instances, the shunting catheter 302 may be made from multiple materials that are reflow soldered together. In certain instances, the shunting catheter 302 may be made from multiple materials that are bonded together with an over mold. In certain embodiments, there may be a portion of the shunting catheter 302 that houses other components of the shunting device 300 that are configured to interact with the patient's anatomy.

In some embodiments, the catheter shaft 304 is reinforced with a braid and can have an etched or casted liner. In certain embodiments, the braid for reinforcing the catheter shaft 304 may be made of nitinol. In some embodiments, the liner may be made from polyetheretherketone (PEEK), polytetrafluoroethylene (PTFE), copolymers of polyamide and polyether, or a combination thereof. In certain embodiments, the catheter shaft 304 may be injection molded or extruded. In some embodiments, the catheter shaft 304 is coated for lubricity with a hydrophilic coating, or other types of coating suitable for coating a catheter shaft as known by a skilled person in the art.

In certain embodiments, the catheter shaft 304 may have multiple lumens. In embodiments, the multiple lumens may allow for the exchange and movement of various parts (for example, the ablation assembly 306, the apposition element 308) during deployment and/or shunting. In certain embodiments, the shunting catheter 302 is used to gain access into a patient's CS, the shunting catheter 302 including multiple lumens to gain access into the patient's LA.

According to some embodiments, the catheter shaft 304 has a distal end 304a and a proximal end (not shown). In some embodiments, the catheter shaft 304 may include a stabilizing element such as distal tip 305 at the distal end 304a that has a curve (for example, a pre-existing curve), for example, a curve conforming to the anatomy of a patient's CS. In embodiments, the distal tip 305 may help with navigation when inserting the shunting catheter 302 into the patient's CS. In certain embodiments, the distal tip 305 may allow for proper positioning of the shunting catheter 302 during shunting. In some instances, the distal tip 305 may be made of a different material than other parts of the catheter shaft 304. In some instances, for example, the distal tip 305 may be made of a material more flexible than the material of other parts of the catheter shaft 304. In some embodiments, the distal tip 305 may be injection molded or machined to have a unique geometry (for example, a curve) for better stabilizing the catheter shaft 304 during deployment.

According to some embodiments, the distal tip 305 may have a length of from about 5 mm to about 85 mm. In certain embodiments, the catheter shaft 304 includes a shaft opening 303. In some embodiments, a portion of the catheter shaft 304 between the shaft opening 303 and the distal end 304a has a curve. In some embodiments, the catheter shaft 304 defines a first axis 307, and the ablation assembly 306 defines a second axis 309 at the second state after deployment. In certain embodiments, the second axis 309 and the first axis 307 form an angle greater than zero degree. In certain embodiments, the second axis 309 and the first axis 307 form an angle greater than 10 degrees.

According to certain embodiments, the catheter shaft 304 includes a shaft lumen 301, and the ablation assembly 306 is disposed in the shaft lumen 301 at a first state (for example, during deployment, during deployment to position of the ablation assembly 306). In certain embodiments, the ablation assembly 306 includes a distal end 306a and a proximal end 306b. In some embodiments, the ablation assembly 306 includes an ablation shaft 312, an ablation mechanism 313, and a puncture element 314. In certain embodiments, the ablation shaft 312 has a pre-determined curve. In certain embodiments, the ablation mechanism 313 is extended from the catheter shaft 304 at the proximal end 306b of the ablation assembly 306 at a second state (for example, a shunting state). In some instances, the ablation assembly 306 extends from the catheter shaft 304 through the shaft opening 303. In certain instances, the puncture element 314 has a diameter (d1) in the range of about 2 millimeters to about 5 millimeters. In some embodiments, once the shunting catheter 302 is in position after deployment, the puncture element 314 may be used to puncture through the wall between a patient's CS and LA.

According to certain embodiments, an energy source coupled to the shunting catheter 302 may provide energy (for example, electrical energy) to the shunting catheter 302, and the shunting catheter 302 may generate and deliver ablation energy (for example, radiofrequency (RF) energy, phased RF energy, cryogenic energy, thermal energy, pulse energy, laser energy, microwave energy, ultrasound energy, and/or the like) to a target location of the patient.

According to some embodiments, the puncture element 314 is disposed at the distal end 306a of the ablation assembly 306. In embodiments, the shaft opening 303 is not at the distal end 304a of the catheter shaft 304. In certain embodiments, the puncture element 314 has a configuration of regular trocar point, regular taper point, regular taper cutting, regular reverse cutting edge, regular diamond point, regular conventual cutting edge, regular blunt taper point, premium lancet point, premium diamond point, or premium cutting edge. In certain embodiments, the puncture element 314 is made of materials including nitinol, stainless steel, cobalt chromium, aluminum, and/or a combination thereof.

In embodiments, the ablation assembly 306 is configured to deliver ablation energy to a target tissue during shunting. In certain embodiments, the ablation energy delivered by the ablation assembly 306 may include radiofrequency (RF) energy, phased RF energy, cryogenic energy, thermal energy, pulse energy, laser energy, microwave energy, ultrasound energy, and/or the like. In certain embodiments, the energy delivered by the ablation assembly 306 punctures through tissue surrounding the target location to create an opening at the target location. In some embodiments, the energy delivered by the ablation assembly 306 ablates tissue surrounding the target location to solidify an opening at the target location. In certain embodiments, delivering energy via the ablation assembly 306 helps prevent tissue regrowth around the created shunt after the procedure.

According to some embodiments, the shunting catheter 302 further includes an outer shaft 318 disposed outside of at least a part of the catheter shaft 304 during deployment. In some embodiments, the outer shaft 318 is made of flexible material that may curve with the anatomy of the patient's CS. In certain embodiments, for example, the outer shaft 318 may include polyether block amide, nylon, silicone, or a combination thereof. In some instances, the outer shaft 318 may be a multi-layered and multi-material component.

In some examples, the outer shaft 318 is reinforced with a braid and can have an etched or casted liner. In some embodiments, the braid for reinforcing the catheter shaft 304 may be made of nitinol. In certain embodiments, the liner may be made from polyetheretherketone (PEEK), polytetrafluoroethylene (PTFE), copolymers of polyamide and polyether, or a combination thereof. In some instances, the outer shaft 318 may include a reinforcing element (for example, a laser-cut tube). In certain embodiments, the outer shaft 318 may be injection molded or extruded. In some embodiments, the catheter shaft 304 is coated for lubricity with a hydrophilic coating, or other types of coating suitable for coating a catheter shaft as known by a skilled person in the art.

In certain examples, the outer shaft 318 and/or the catheter shaft 304 may house all of the catheter components until the desired target location is reached. In some embodiments, once the shunting catheter 302 has reached the target location, the outer shaft 318 may translate towards the proximal end of the catheter shaft 304 to expose the ablation assembly 306 and other components.

According to certain embodiments, the apposition element 308 is disposed within the outer shaft 318 at a first state (for example, during deployment). In embodiments, the apposition element 308 protrudes from the catheter shaft 304 during deployment. In certain embodiments, the apposition element 308 is flexible and compressed to fit within the outer shaft 318, and configured to decompress and protrude from the catheter shaft 304 during deployment. In some embodiments, the apposition element 308 is disposed proximate to the ablation assembly 306 and/or the one or more shaft openings 303. In some instances, the apposition element 308 is a braided structure including one or more nickel titanium wires. In some instances, the apposition element 308 is made of a flexible material having a portion protruding from the catheter shaft 304. In some examples, the flexible material may be a foam. In some instances, the flexible material may be a balloon filled with a contrast solution that is visible under fluoroscopy. In some instances, the flexible material may be a polymer with a radiopaque marker added for visualization. In some embodiments, the radiopaque marker may include tantalum, gold, or any radiopaque maker known by a skilled person in the art.

In certain embodiments, the apposition element 308 is configured to appose at least one wall in a patient's cardiovascular system (for example, CS, LA, etc.) such that the shunting catheter 302 is stabilized in one position once deployed. In some embodiments, the apposition element 308 is configured to appose two or more walls in a patient's cardiovascular system. According to some embodiments, the apposition element 308 has several benefits, one of which is the stabilization of catheter 302 after deployment. In some embodiments, any movement or lack thereof the protruding element (for example, a braided element) provides an estimated distance of how far the catheter 302 is away from the vessel wall of patient's CS. In addition, in instances where the apposition element 308 includes a braided element, such that when the braided element is apposing the vessel wall of a patient's CS, the openings between the braids still allow blood flow through the apposition element 308, thus reducing the risk of thrombus formation caused by any occlusion in the vessel.

The apposition element 308 may be made of nitinol, and is reflow soldered or bonded to the catheter shaft 304. In some embodiments, the apposition element 308 serves the purpose of pushing against back wall of a patient's CS, to allow for the shunting catheter 302 to translate forward and against target location on a wall between patient's CS and LA. In certain embodiments, the apposition element 308 may include an elastic braided structure, and may thus expand and compress with force applied by the outer shaft 318, or through other mechanical means.

In some embodiments, for example as shown, the apposition element 308 is disposed on the same side of the catheter shaft 304 as the ablation assembly 306. In some embodiments, the apposition element 308 may be on an opposite side of the catheter shaft 304 from the ablation assembly 306. In certain embodiments, the apposition element 308 may be configured to appose the wall between patient's CS and LA, instead of the back of patient's CS wall. In certain embodiments, this may allow the shunting device 300 to then penetrate through the patient's CS wall to gain access into the patient's LA. In embodiments, the apposition element 308 helps stabilize and position the shunting catheter 302 in the patient's CS at a target location.

Figures 4A, 4B:
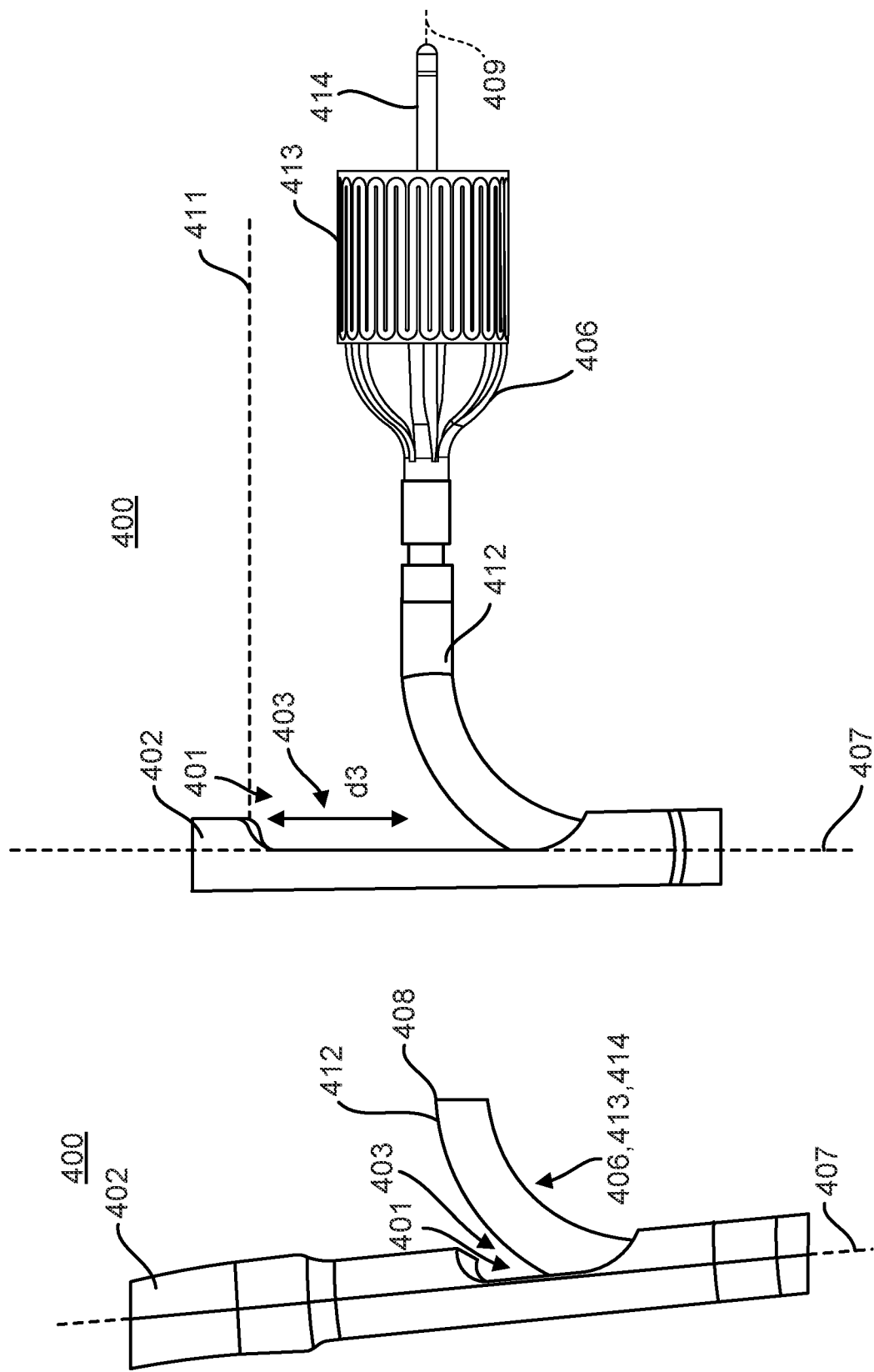
FIGS. 4A-4B are schematic diagrams of side views of an example of a shunting catheter, in accordance with embodiments of the present disclosure.

FIGS. 4A-4B are schematic diagrams of side views of an example of a shunting catheter 400, in accordance with embodiments of the present disclosure. In some embodiments and as shown in FIGS. 4A-4B, the shunting catheter 400 includes a catheter shaft 402 having a shaft lumen 401, a shaft opening 403, and an ablation assembly 406 disposed within the shaft lumen 401 at a first state (for example, during deployment to position the ablation assembly 406, as shown in FIG. 4A), and extended from the catheter shaft 402 at a second state (for example, during shunting, as shown in FIG. 4B). In some embodiments, the ablation assembly 406 includes a crimping shaft 412 having a predetermined curve for an ablation mechanism 413 to deploy, and a puncture element 414.

According to some embodiments, the ablation assembly 406 may have a telescoping feature (for example, the ablation mechanism 413 and the puncture element 414 being retractable into the crimping shaft 412, as shown in FIG. 4A) to allow the blunt distal end 408 of the crimping shaft 412 to contact the wall between the patient's LA and CS, or the patient's AS, before the puncture element 414 is translated forward to make contact with the wall between the patient's LA and CS, or the patient's AS. In embodiments, the telescoping feature of the ablation assembly 406 allows for a safe delivery of the puncture element 414 to the target location.

According to certain embodiments, the ablation assembly 406 of the shunting catheter 400 has a first deployment state (for example, shown in FIG. 4A) and a second deployment state (for example, shown in FIG. 4B). In some embodiments, at the first deployed state the ablation mechanism 413 and the puncture element 414 are retracted in a lumen of the crimping shaft 412. In some embodiments, at the second deployed state the ablation mechanism 413 and the puncture element 414 are extended from a distal end 408 of the crimping shaft 412.

In certain embodiments, the shaft opening 403 includes an edge defining an opening axis 411. In some embodiments, the opening axis 411 may be generally perpendicular to a first axis 407 along the catheter shaft 402. In some embodiments, the distance (d3) between the opening axis 411 and a second axis 409 along the ablation assembly 406 may be from about 3 mm to about 20 mm.

Figure 5A:
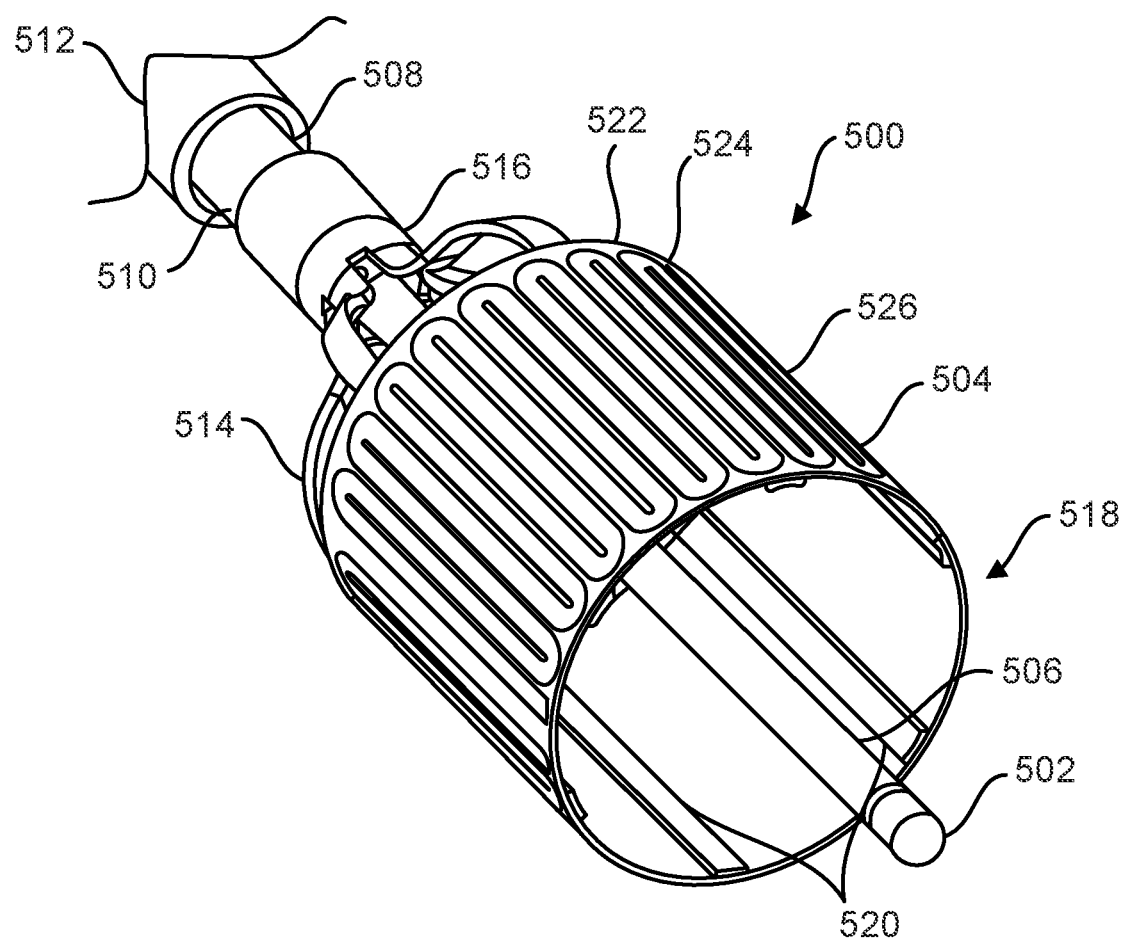
FIGS. 5A-5C are schematic diagrams of views of an example of an ablation assembly, in accordance with embodiments of the present disclosure.
Figure 5B:
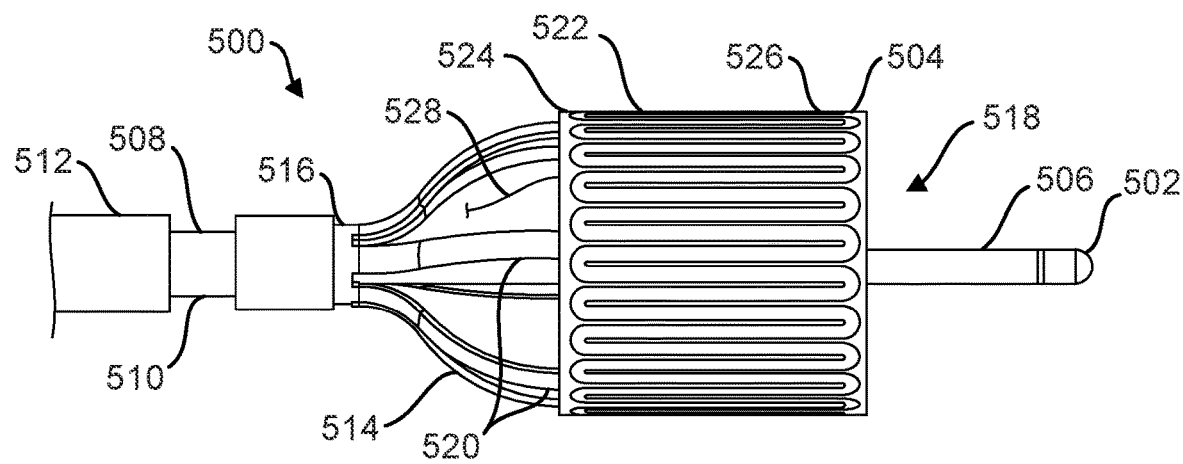
Figure 5C:
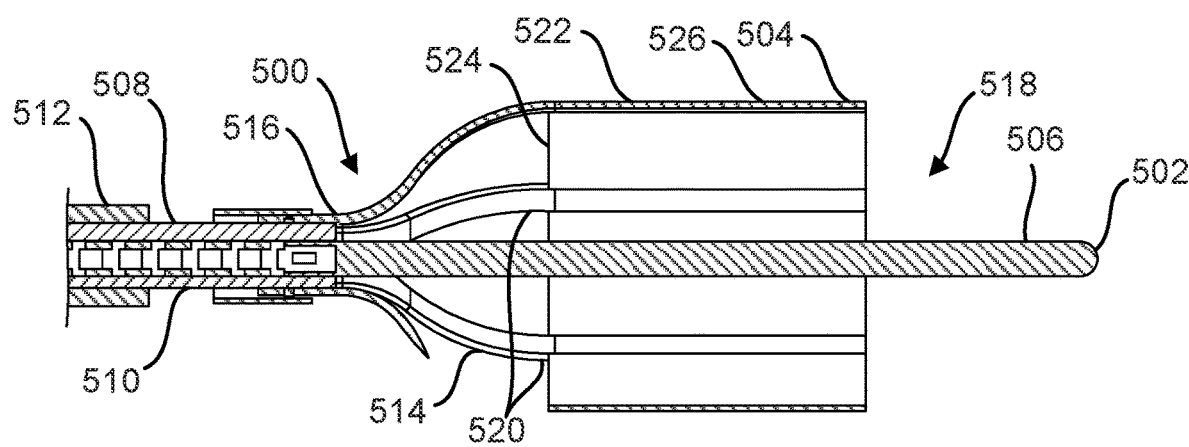

FIGS. 5A-5C are schematic diagrams of views of an example of an expandable ablation assembly 500, in accordance with embodiments of the present disclosure. In certain embodiments, the ablation assembly 500 may include a puncture element 502 and an ablation mechanism 504. In some embodiments, the puncture element 502 is coupled to a distal end of an inner member 506, more specifically a laser-cut tube, of an ablation shaft 508. In some embodiments, the puncture element 502 may be configured to puncture an opening at a target location in a patient, such as a vessel wall, more specifically the wall between the CS and LA of the patient, or the AS of the patient. In certain embodiments, the ablation mechanism 504 has a length in a range of 3 mm to 15 mm. In certain embodiments, the ablation mechanism 504 has an expanded diameter in a range of 2 mm to 10 mm.

According to some embodiments, the puncture element 502 (for example, a needle) may take on many different needle configurations. Configurations for the puncture element 502 may include, but not are not limited to, regular trocar point, regular taper point, regular taper cutting, regular reverse cutting edge, regular diamond point, regular conventual cutting edge, regular blunt taper point, premium lancet point, premium diamond point, and/or premium cutting edge. In certain embodiments, the puncture element 502 is made of materials including nitinol, stainless steel, cobalt chromium, aluminum, and/or a combination thereof. In certain embodiments, the puncture element 502 physically contacts tissue to puncture an opening at the target location in the patient. In certain embodiments, the puncture element 502 receives energy from an energy source and delivers ablation energy (such as radiofrequency (RF) energy, phased RF energy, cryogenic energy, thermal energy, pulse energy, laser energy, ultrasound energy, microwave energy, and/or the like) to tissue to puncture an opening at the target location in the patient.

The ablation mechanism 504 is disposed on and/or within an outer member 510 of the ablation shaft 508, and the ablation mechanism 504 and the ablation shaft 508 are together slidable into and out of a lumen of a crimping shaft 512. In certain embodiments, after the puncture element 502 forms an opening in the tissue at a target location in a patient, the ablation mechanism 504 expands to enlarge the opening in the tissue. In some embodiments, the ablation mechanism 504 then receives energy from an energy source and delivers ablation energy (such as radiofrequency (RF) energy, phased RF energy, cryogenic energy, thermal energy, pulse energy, laser energy, ultrasound energy, microwave energy, and/or the like) to ablate the tissue and thereby solidify the opening at the target location.

In some embodiments, the ablation mechanism 504 includes an expandable cage 514, and the expandable cage 514 is fixedly coupled at its proximal end 516 to the ablation shaft 508 (for example, via reflow soldering or adhesives). In certain embodiments, the expandable cage 514 illustratively includes an open distal end 518 (that is, being disposed apart from the inner member 506 of the ablation shaft 508). Alternatively, the expandable cage 514 may taper toward the distal end 518 and movably couple to the inner member 506 of the ablation shaft 508 at the distal end 518. As another alternative, the expandable cage 514 may taper toward the distal end 518, fixedly couple to the inner member 506 of the ablation shaft 508 at the distal end 518, and movably couple to the inner member 506 of the ablation shaft 508 at the proximal end 516.

In certain embodiments, the expandable cage 514 is made of one or more materials that facilitate self-expansion, such as nitinol, or one or more other materials, such as stainless steel, titanium, platinum-iridium, or cobalt-chromium.

In certain embodiments and as illustrated, the expandable cage 514 includes a plurality of expandable struts 520. In some embodiments, the struts 520 are collapsed radially inwardly, or toward each other, when the ablation mechanism 504 is disposed in the crimping shaft 512 (that is, in a first state; not specifically illustrated). In certain embodiments, the struts 520 expand radially outwardly, or away from each other, when the ablation mechanism is disposed outside of the crimping shaft 512 (that is, in a second state, as illustrated in FIGS. 5A-5C). In certain embodiments and as illustrated, the expandable cage 514 includes six expandable struts 520. In other embodiments, the expandable cage 514 includes a different number of expandable struts 520, such as two, three, four, five, seven, eight, nine, ten, or more expandable struts 520. In certain embodiments and as illustrated, the struts 520 are self-expanding (for example, by being made of a shape memory material and set in the expanded state). In certain embodiments, the self-expansion of the struts 520 may be controlled by a constrainer, such as a plurality of sutures (for example, thin strands) coupled to the struts 520. Such a constrainer may be reconfigured from a constraining state to a release state to permit the struts 520 to expand, and the constrainer may be reconfigured from the release state to the constraining state to collapse the struts 520. In some embodiments, the constrainer may be coupled to distal ends of the struts. In certain embodiments, the struts 520 are expanded by an actuator, such as an inflatable balloon (not shown). In certain embodiments, an actuator may be disposed in a cavity of the cage 514 formed between the struts 520. In certain embodiments, one or more additional components, such as control wires coupled to the actuators, may be disposed in the cavity of the cage 514 and extend through the ablation shaft 508. In certain embodiments, such as those in which the distal end 518 of the expandable cage 514 fixedly couple to the inner member 506 of the ablation shaft 508 and the proximal end 516 movably couples to the inner member 506 of the ablation shaft 508, the actuator may be a slidable intermediate shaft (not shown).

In certain embodiments and as illustrated, the expandable cage 514 carries an electrode structure 522 including one or more electrodes. In some embodiments, the electrode structure 522 may include a thin film electrode. In some embodiments, the electrode structure 522 includes a thin film substrate and one or more electrodes are disposed on the thin film substrate. In certain embodiments, the one or more electrodes includes two or more electrodes. In some embodiments, at least two of the one or more electrodes form an electrode pair. In certain embodiments, the electrode structure 522 has a length in a range of 4 mm to 12 mm. In certain embodiments, the electrode structure 522 has an expanded diameter in a range of 2 mm to 10 mm. In certain embodiments, the electrode structure 522 includes a base 524 that carries one or more conductors 526. In some embodiments, the base 524 is made of a flexible/foldable material (such as an insulating polymer, more specifically a polyimide) and thereby moves with the expandable cage 514 from the first state to the second state and vice versa.

In some embodiments and as illustrated, the conductor 526 is carried on an outer surface of the base 524, and the conductor 526 is configured to contact tissue at a target location in a patient and deliver ablation energy to the tissue. In certain embodiments, the conductor 526 is made of one or more conductive metals, such as gold, platinum-iridium, copper, or the like. In certain embodiments and as illustrated, the conductor 526 includes a serpentine shape, more specifically, the conductor 526 includes longitudinally extending segments joined by short turns near the longitudinal ends of the base 524. In certain embodiments, the conductor 526 may have different shapes, although conductors 526 having serpentine shapes may experience lower strain upon expansion and contraction relative to other shapes.

In certain embodiments, one or more lead wires 528 (FIG. 5B) couple the conductor 526 to an energy source. In some embodiments, the lead wires 528 may extend through one of the shafts (for example, the crimping shaft 512 or the ablation shaft 508) or outside of the shafts.

In alternative embodiments, the expandable cage 514 carries a plurality of electrodes. In alternative embodiments, the ablation mechanism 504 lacks the electrode structure 522, and the expandable struts 520 instead contact tissue at a target location within a patient and act as electrodes to deliver ablation energy to the tissue. In such embodiments, one or more portions of the expandable struts 520 may carry an insulating coating (such as polyether ether ketone (PEEK), expanded polytetrafluoroethylene (ePTFE), elastomeric coatings, or the like) to inhibit delivery of ablation energy to the blood of the patient.

Figure 6A:
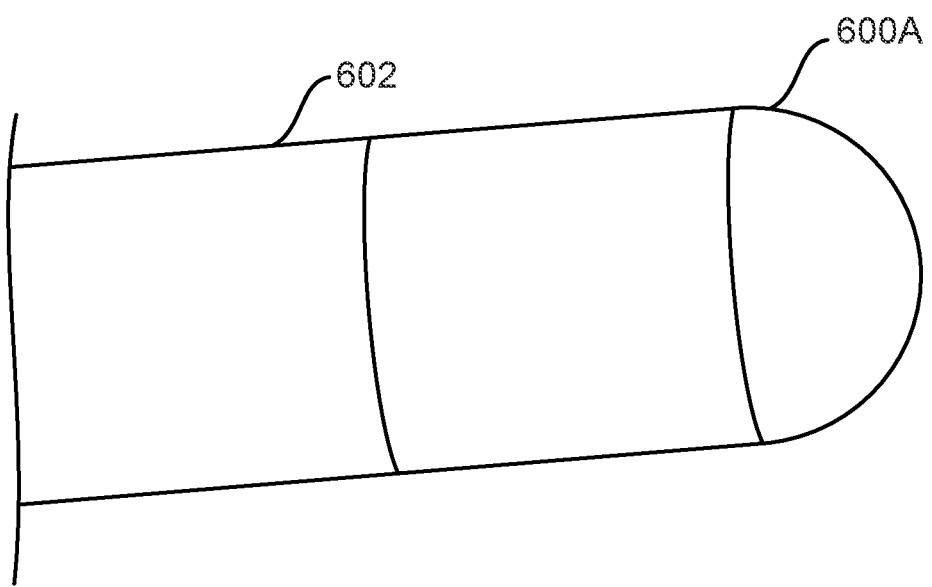
FIGS. 6A-6B are schematic diagrams of side views of examples of puncture elements and inner members of ablation shafts, in accordance with embodiments of the present disclosure.
Figure 6B:
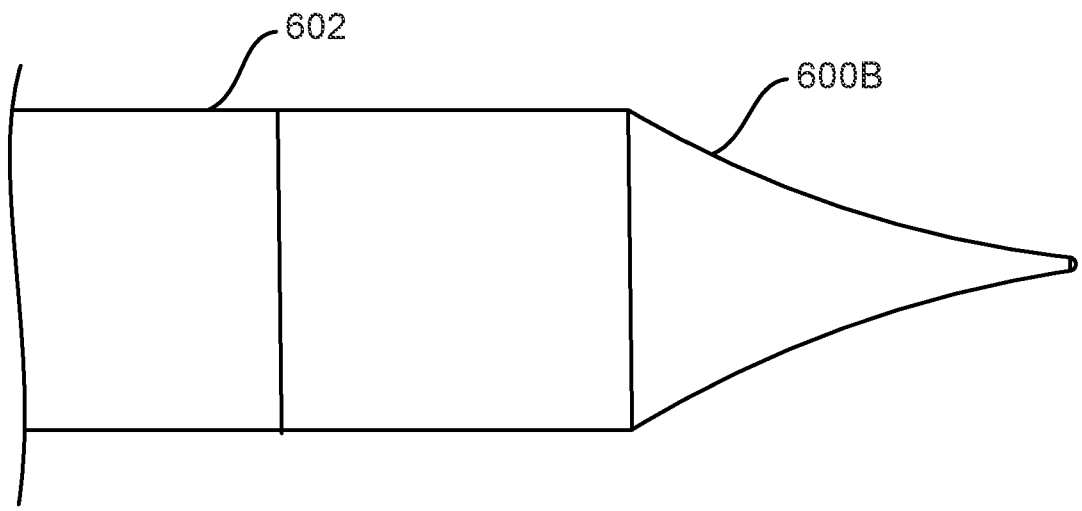

FIGS. 6A-6B are schematic diagrams of side views of examples of puncture elements 600A and 600B of ablation assemblies and inner members 602 of ablation shafts, in accordance with embodiments of the present disclosure. In certain embodiments, the puncture elements 600A and 600B and the inner members 602 are made of materials including nitinol, stainless steel, cobalt chromium, aluminum, and/or a combination thereof. In some embodiments, the puncture elements 600A and 600B may be coupled to the inner members 602 of the ablation shafts in various manners, such as via laser welding. In certain embodiments, the puncture elements 600A and 600B and the inner members 602 of the ablation shafts may have outer diameters in a range of 0.06 in. to 0.08 in., more specifically about 0.07 in. In some embodiments, the puncture elements 600A and 600B may be coupled to pull wires (not shown) to facilitate bending and steering of the inner members 602 of the ablation shafts.

According to some embodiments, for example as shown in FIG. 6A, the puncture element 600A has a rounded tip shape. In certain embodiments, the puncture element 600A has a hemispherical tip shape. Such a tip shape may facilitate delivering ablation energy (such as radiofrequency (RF) energy, phased RF energy, cryogenic energy, thermal energy, pulse energy, laser energy, ultrasound energy, microwave energy, and/or the like) to ablate tissue at a target location within a patient (for example, the wall between the patient's LA and CS, or the patient's AS).

According to some embodiments, for example as shown in FIG. 6B, the puncture element 600B has a pointed tip shape. In certain embodiments, the puncture element 600B includes a regular trocar pointed shape. Such a tip shape may facilitate physically contacting tissue to puncture an opening at a target location within a patient (for example, the wall between the patient's LA and CS, or the patient's AS).

Figure 7:
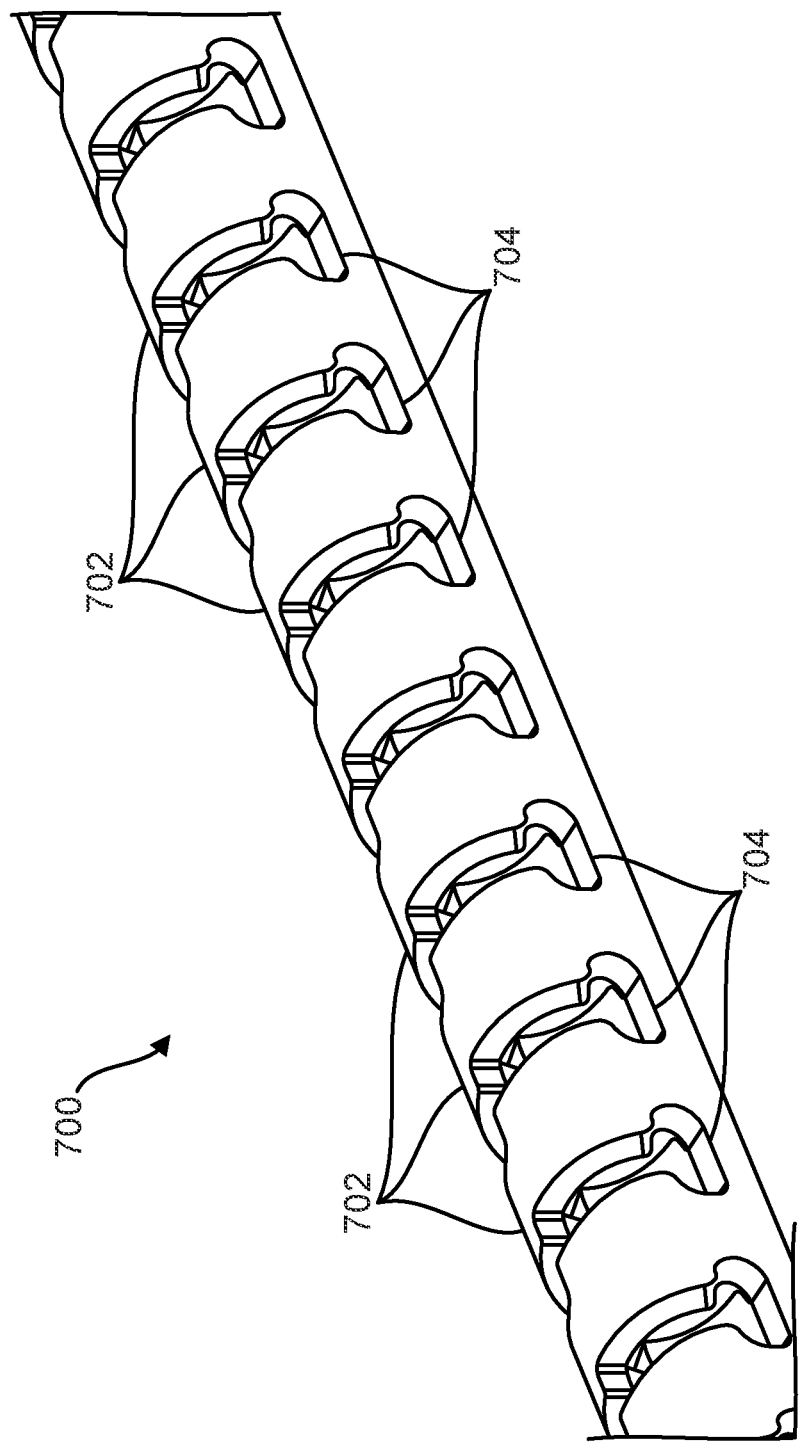
FIG. 7 is a schematic diagram of a perspective view of an example of an inner member of an ablation shaft, in accordance with embodiments of the present disclosure.

FIG. 7 is a schematic diagram of a perspective view of an example of an inner member 700 of an ablation shaft, in accordance with embodiments of the present disclosure. In certain embodiments, the inner member 700 is made of materials including nitinol, stainless steel, cobalt chromium, aluminum, and/or a combination thereof. In certain embodiments, the inner member 700 is bendable and steerable via one or more pull wires (not shown). In some embodiments, to facilitate such bending and steering, the inner member 700 may be hollow and include a plurality of ribs 702 separated by voids 704. In alternative embodiments, the inner member 700 may have a different structure.

Figure 8A:
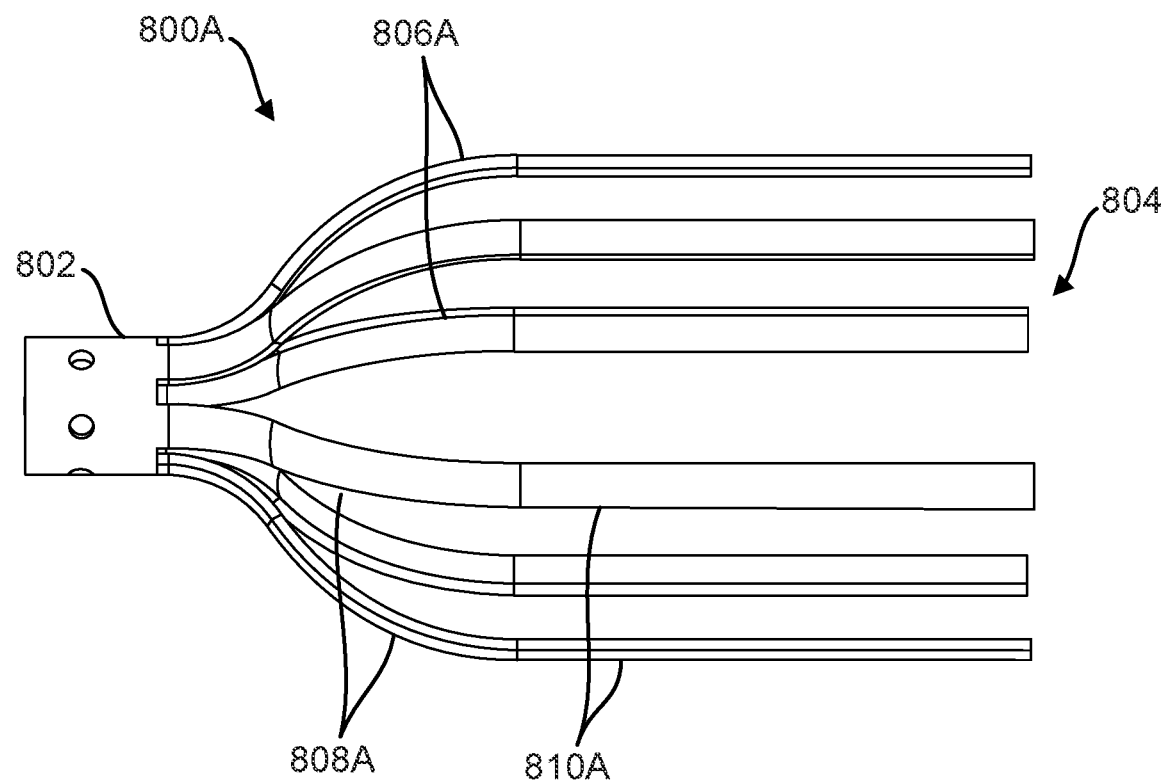
FIGS. 8A-8B are schematic diagrams of side views of examples of expandable cages, in accordance with embodiments of the present disclosure.
Figure 8B:
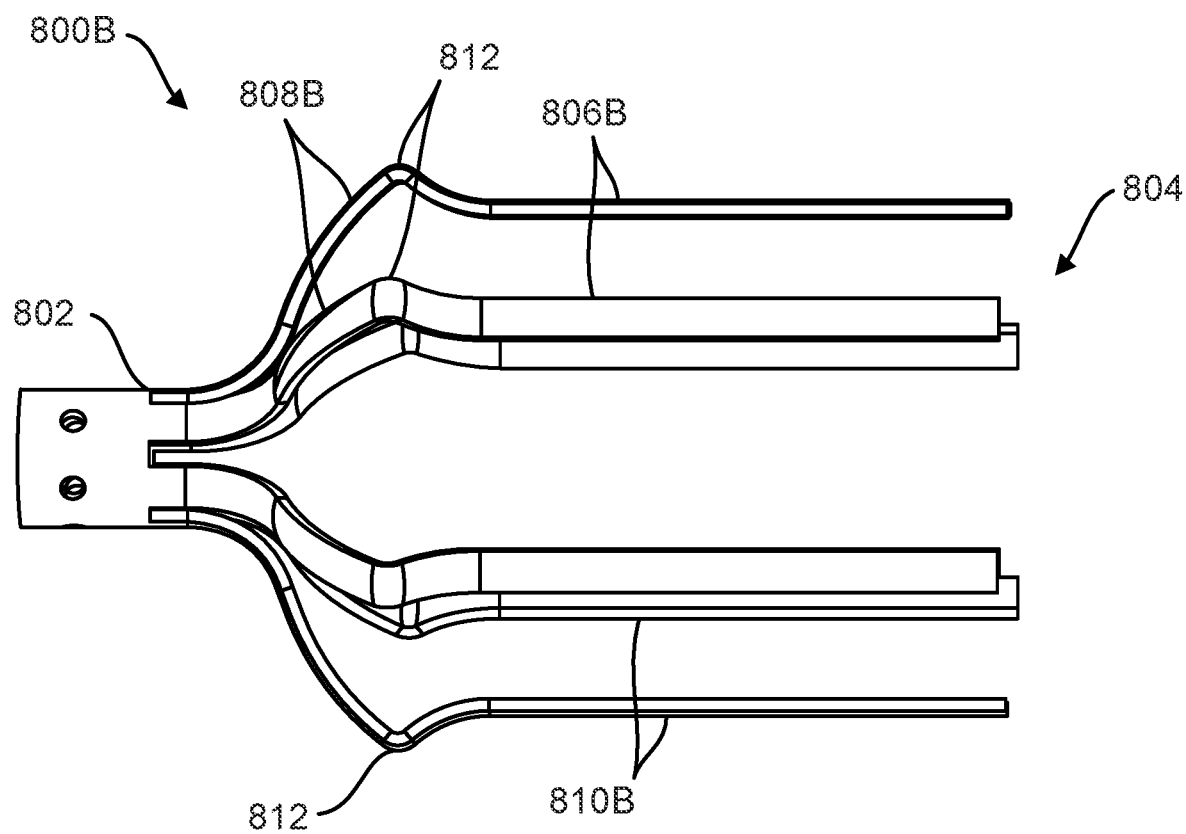

FIGS. 8A-8B are schematic diagrams of side views of examples of expandable cages 800A and 800B of ablation assemblies, in accordance with embodiments of the present disclosure. In certain embodiments, the expandable cages 800A and 800B carry one or more electrodes for receiving energy from an energy source and delivering ablation energy to tissue at a target location in a patient. In certain embodiments, the expandable cages 800A and 800B contact tissue at a target location in a patient and act as electrodes to deliver ablation energy to the tissue. In such embodiments, one or more portions of the expandable cages 800A and 800B may carry an insulating coating (such as polyether ether ketone (PEEK), expanded polytetrafluoroethylene (ePTFE), elastomeric coatings, or the like) to inhibit delivery of ablation energy to certain parts of the anatomy or the blood of the patient.

In certain embodiments, the expandable cages 800A and 800B are made of one or more materials that facilitate self-expansion, such as nitinol, or one or more other materials, such as stainless steel, titanium, platinum-iridium, or cobalt-chromium. In certain embodiments, the expandable cages 800A and 800B include proximal collars 802 for coupling to ablation shafts. In some embodiments and as illustrated, the expandable cages 800A and 800B include open distal ends 804 (that is, being disposed apart from ablation shafts). Alternatively, the expandable cages 800A and 800B may taper toward distal collars that movably couple to ablation shafts.

According to certain embodiments, the expandable cages 800A and 800B include a plurality of expandable struts 806A and 806B. In certain embodiments and as illustrated, the expandable cages 800A and 800B each include six expandable struts 806A and 806B. In other embodiments, the expandable cages 800A and 800B include a different number of expandable struts 806A and 806B, such as two, three, four, five, seven, eight, nine, ten, or more expandable struts 806A and 806B.

According to some embodiments, for example as shown in FIG. 8A, the expandable struts 806A of the cage 800A each include a flared portion 808A and a longitudinally extending portion 810A. In certain embodiments, the longitudinally extending portions 810A together define the maximum diameter of the expanded cage 800A.

According to some embodiments, for example as shown in FIG. 8B, the expandable struts 806B of the cage 800B each include a flared portion 808B and a longitudinally extending portion 810B. In some embodiments, each flared portion 808B extends outwardly to an elbow 812, and the elbows 812 together define the maximum diameter of the expanded cage 800B. In certain embodiments, the elbows 812 inhibit a crimping shaft from binding on an electrode carried by the cage 800B when the crimping shaft slides over and compresses the cage 800B and the electrode from an expanded state to a compressed state.

Figure 9A:
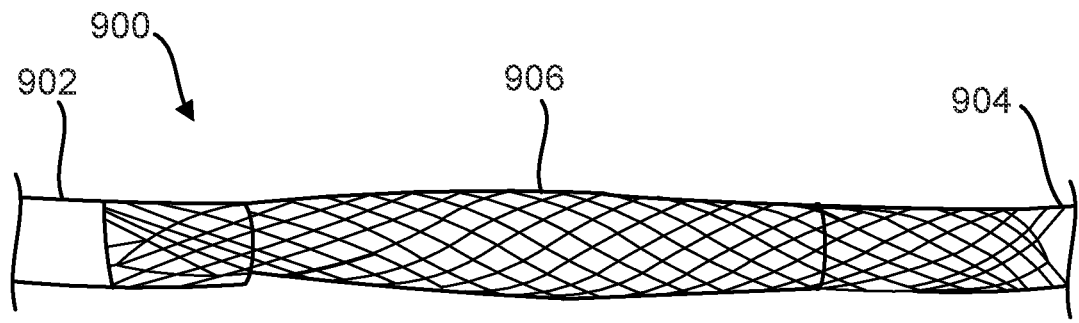
FIGS. 9A-9B are schematic diagrams of side views of another example of an expandable cage, in accordance with embodiments of the present disclosure.
Figure 9B:
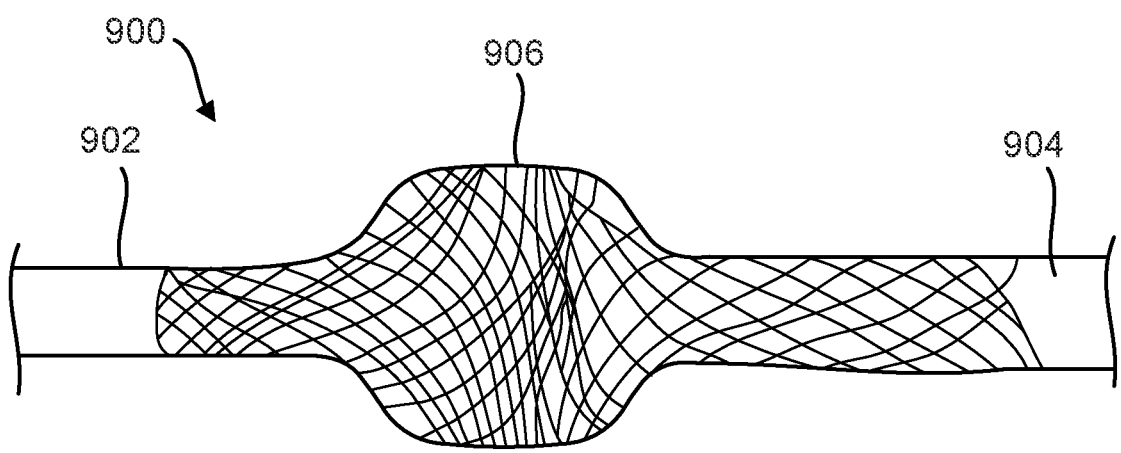

FIGS. 9A-9B are schematic diagrams of side views of an example of an expandable cage 900 of an ablation assembly, in accordance with embodiments of the present disclosure. FIG. 9A illustrates the expandable cage 900 in a first state or compressed state, and FIG. 9B illustrates the expandable cage 900 in a second state or expanded state. In certain embodiments, the expandable cage 900 carries one or more electrodes for receiving energy from an energy source and delivering ablation energy to tissue at a target location in a patient. In certain embodiments, the expandable cage 900 contacts tissue at a target location in a patient and acts as an electrode to deliver ablation energy to the tissue. In such embodiments, one or more portions of the expandable cage 900 may carry an insulating coating (such as polyether ether ketone (PEEK), expanded polytetrafluoroethylene (ePTFE), elastomeric coatings, or the like) to inhibit delivery of ablation energy to the blood of the patient.

In certain embodiments, the expandable cage 900 is made of one or more materials that facilitate self-expansion, such as nitinol, or one or more other materials, such as stainless steel, titanium, platinum-iridium, or cobalt-chromium. In certain embodiments, the expandable cage 900 includes a proximal collar 902 and a distal collar 904 for coupling to an ablation shaft. In other embodiments, the expandable cage 900 lacks the distal collar 904 and includes an open distal end (that is, being disposed apart from an ablation shaft).

The expandable cage 900 includes a plurality of expandable struts, more specifically a plurality of braided wires 906. In certain embodiments and as illustrated, the braided wires 906 may generally include a first set of wires that extend helically in a first direction and a second set of wires that extend helically in a second, opposite direction. Alternatively, the braided wires 906 may have different arrangements.

Figure 10:
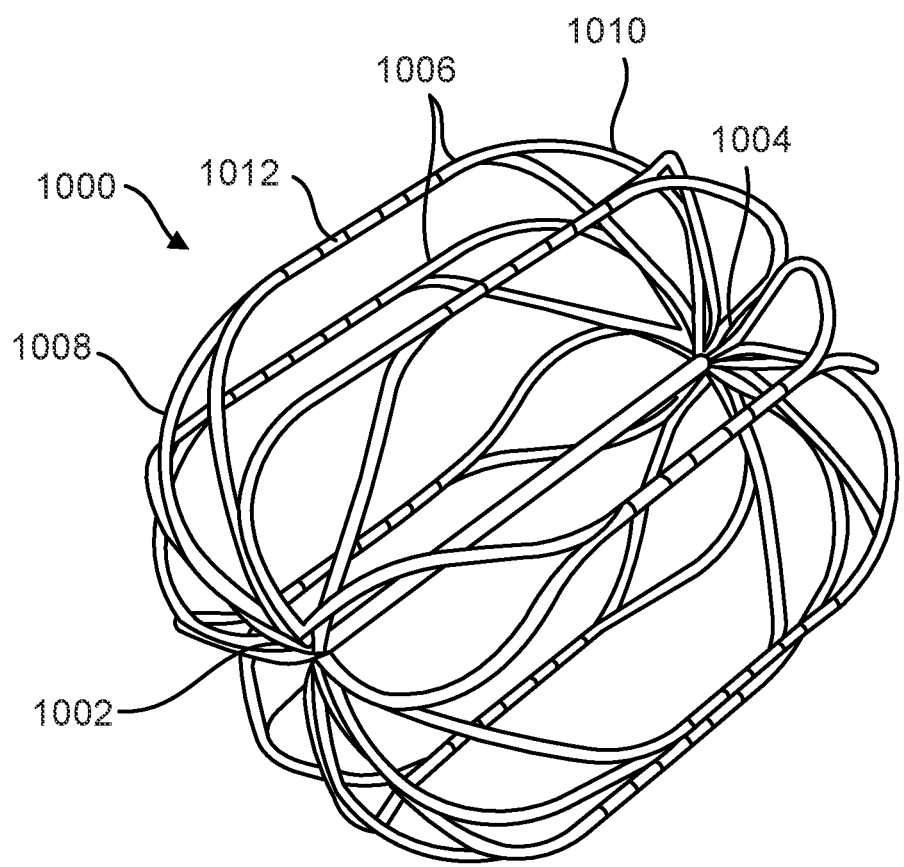
FIG. 10 is a schematic diagram of a perspective view of another example of an expandable cage, in accordance with embodiments of the present disclosure.

FIG. 10 is a schematic diagram of a perspective view of an example of an expandable cage 1000 of an ablation assembly, in accordance with embodiments of the present disclosure. In certain embodiments, the expandable cage 1000 carries one or more electrodes for receiving energy from an energy source and delivering ablation energy to tissue at a target location in a patient. In certain embodiments, the expandable cage 1000 contacts tissue at a target location in a patient and acts as an electrode to deliver ablation energy to the tissue. In such embodiments, one or more portions of the expandable cage 1000 may carry an insulating coating (such as polyether ether ketone (PEEK), expanded polytetrafluoroethylene (ePTFE), elastomeric coatings, or the like) to inhibit delivery of ablation energy to the blood of the patient.

In certain embodiments, the expandable cage 1000 is made of one or more materials that facilitate self-expansion, such as nitinol, or one or more other materials, such as stainless steel, titanium, platinum-iridium, or cobalt-chromium. In certain embodiments, the expandable cage 1000 includes a distal hub 1002 and a proximal hub 1004 for coupling to an ablation shaft. In other embodiments, the expandable cage 1000 lacks the distal hub 1002 and includes an open distal end (that is, being disposed apart from an ablation shaft).

The expandable cage 1000 include a plurality of expandable struts 1006. In certain embodiments and as illustrated, the expandable cage 1000 includes eight expandable struts 1006. In other embodiments, the expandable cage 1000 includes a different number of expandable struts 1006, such as two, three, four, five, six, seven, nine, ten, or more expandable struts 1006. In certain embodiments, each expandable strut 1006 includes a proximal loop 1008, a distal loop 1010, and a longitudinally extending portion 1012 coupling the loops 1008 and 1010. In other embodiments, the expandable struts 1006 have different structures.

Figure 11:
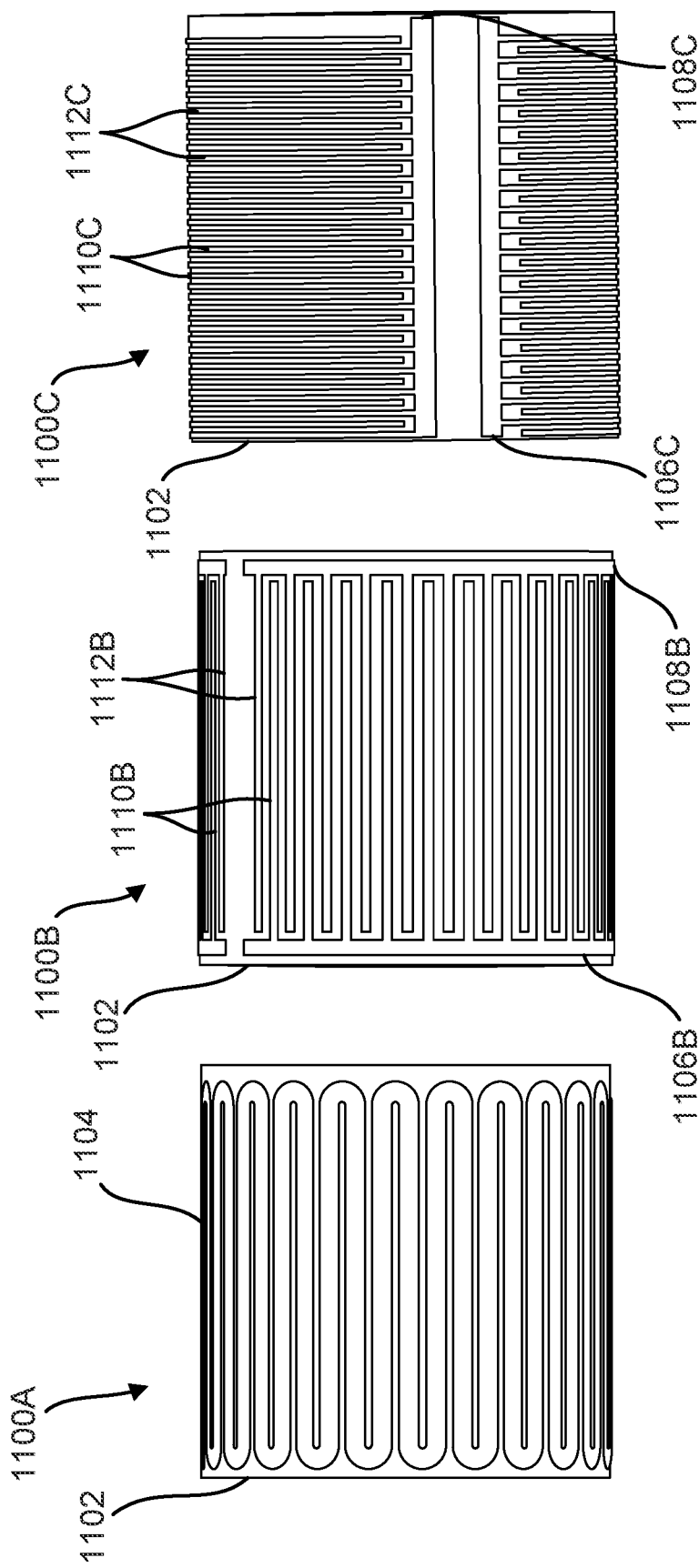
FIGS. 11A-11C are schematic diagrams of side views of examples of electrodes, in accordance with embodiments of the present disclosure.

FIGS. 11A-11C are schematic diagrams of side views of examples of electrode structures 1100A, 1100B, and 1100C of ablation assemblies, in accordance with embodiments of the present disclosure. In some embodiments, the electrode structures 1100A, 1100B, and 1100C are configured to receive energy from an energy source and deliver ablation energy to tissue at a target location in a patient. In certain embodiments, each electrode structure 1100A, 1100B, and 1100C includes one or more electrodes. In some embodiments, each electrode structure 1100A, 1100B, and 1100C includes a thin film electrode. In some embodiments, each electrode structure 1100A, 1100B, and 1100C includes a thin film substrate and one or more electrodes are disposed on the thin film substrate. In certain embodiments, the one or more electrodes includes two or more electrodes. In some embodiments, at least two of the one or more electrodes form an electrode pair.

Each electrode structure 1100A, 1100B, and 1100C includes a base 1102 that carries one or more conductors. In certain embodiments, the base 1102 is made of a flexible/foldable material (such as an insulating polymer, more specifically a polyimide) and is movable from a first state or compressed state to a second state or expanded state and vice versa. In some embodiments, the conductor is made of one or more conductive metals, such as gold, platinum-iridium, copper, or the like.

According to some embodiments, for example as shown in FIG. 11A, the base 1102 may carry a single conductor 1104. In certain embodiments, the conductor 1104 includes a serpentine shape, more specifically, the conductor 1104 includes longitudinally extending segments joined by short turns near the longitudinal ends of the base 1102. Such a shape may cause the conductor 1104 to experience lower strain upon expansion and contraction relative to other shapes. In certain embodiments, the electrode structure 1100A has a length in a range of 4 mm to 12 mm. In certain embodiments, the electrode structure 1100A has an expanded diameter in a range of 2 mm to 10 mm.

According to some embodiments, for example as shown in FIG. 11B, the base 1102 may carry a first conductor 1106B and a second conductor 1108B. In some embodiments, the first conductor 1106B includes a plurality of longitudinally extending first fingers 1110B, the second conductor 1108B includes a plurality of longitudinally extending second fingers 1112B, the first fingers 1110B being interdigitated with the second fingers 1112B. In certain embodiments, such an arrangement of interdigitated conductor fingers facilitates more uniform tissue ablation than other conductor arrangements. In certain embodiments, the first fingers 1110B and the second fingers 1112B have a width in a range of 0.002 in. to 0.010 in. In certain embodiments, the first fingers 1110B and the second fingers 1112B are spaced apart by a distance in a range of 0.002 in. to 0.010 in. In certain embodiments, the electrode structure 1100B has a length in a range of 4 mm to 12 mm. In certain embodiments, the electrode structure 1100B has an expanded diameter in a range of 2 mm to 10 mm.

According to some embodiments, for example as shown in FIG. 11C, the base 1102 may carry a first conductor 1106C and a second conductor 1108C. In some embodiments, the first conductor 1106C includes a plurality of circumferentially extending first fingers 1110C, the second conductor 1108C includes a plurality of circumferentially extending second fingers 1112C, the first fingers 1110C being interdigitated with the second fingers 1112C. In certain embodiments, such an arrangement of interdigitated conductor fingers facilitates more uniform tissue ablation than other conductor arrangements. In certain embodiments, the first fingers 1110C and the second fingers 1112C have a width in a range of 0.002 in. to 0.010 in. In certain embodiments, the first fingers 1110C and the second fingers 1112C are spaced apart by a distance in a range of 0.002 in. to 0.010 in. In certain embodiments, the electrode structure 1100C has a length in a range of 4 mm to 12 mm. In certain embodiments, the electrode structure 1100C has an expanded diameter in a range of 2 mm to 10 mm.

Figure 12:
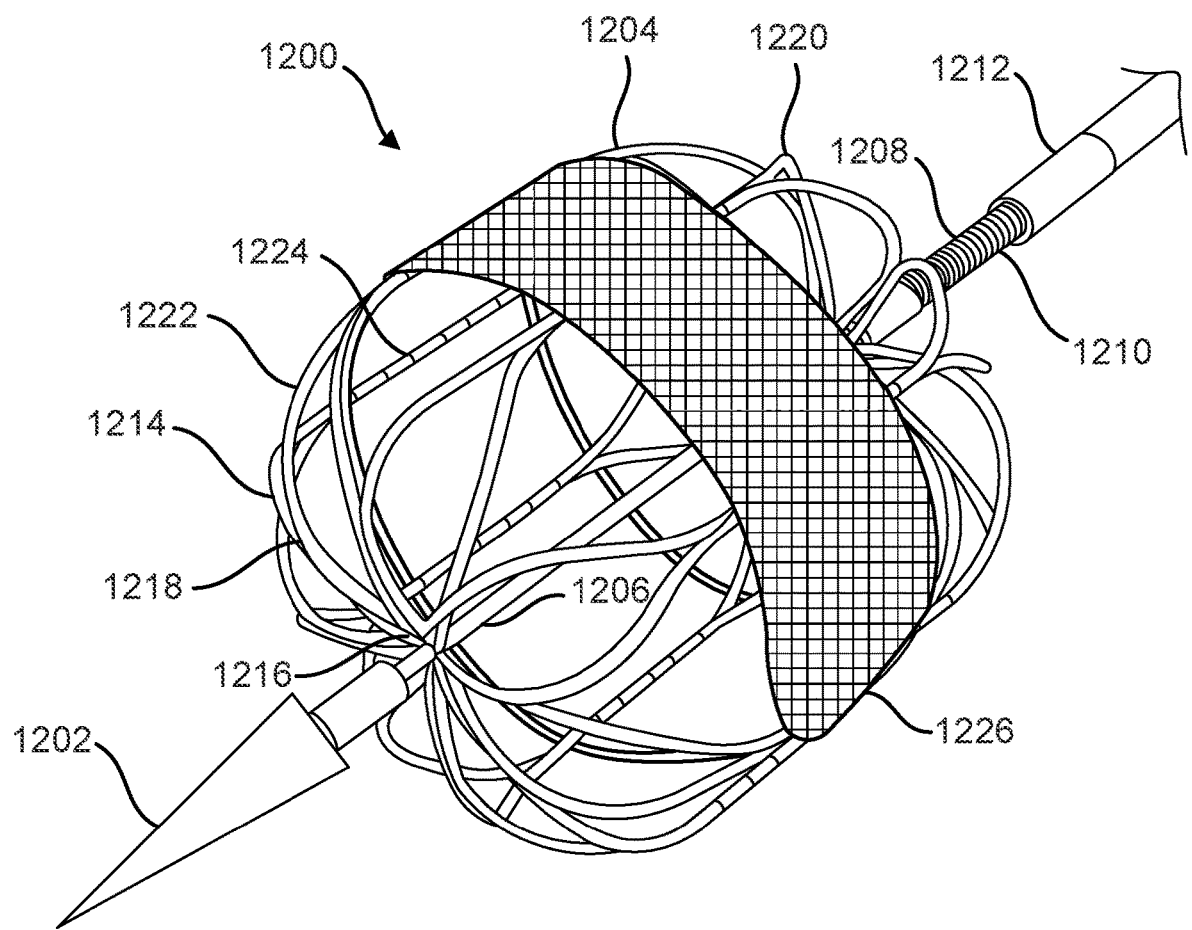
FIG. 12 is a schematic diagram of a perspective view of an example of an ablation assembly, in accordance with embodiments of the present disclosure.

FIG. 12 is a schematic diagram of a perspective view of an example of an expandable ablation assembly 1200 in an expanded state, in accordance with embodiments of the present disclosure. In some embodiments, the ablation assembly 1200 may include a puncture element 1202 and an ablation mechanism 1204. In certain embodiments, the puncture element 1202 is coupled to a distal end of an inner member 1206 of an ablation shaft 1208. In some embodiments, the puncture element 1202 may be configured to puncture an opening at a target location in a patient, such as a vessel wall, more specifically the wall between the CS and LA of the patient, or the AS of the patient. In certain embodiments, the ablation mechanism 1204 has a length in a range of 3 mm to 15 mm. In certain embodiments, the ablation mechanism 1204 has an expanded diameter in a range of 2 mm to 10 mm.

According to some embodiments, the puncture element 1202 (for example, a needle) may take on many different needle configurations. Configurations for the puncture element 1202 may include, but are not limited to, regular trocar point, regular taper point, regular taper cutting, regular reverse cutting edge, regular diamond point, regular conventual cutting edge, regular blunt taper point, premium lancet point, premium diamond point, and/or premium cutting edge. In certain embodiments, the puncture element 1202 is made of materials including nitinol, stainless steel, cobalt chromium, aluminum, and/or a combination thereof. In certain embodiments, the puncture element 1202 physically contacts tissue to puncture an opening at the target location in the patient. Additionally or alternatively, the puncture element 1202 receives energy from an energy source and delivers ablation energy (such as radiofrequency (RF) energy, phased RF energy, cryogenic energy, thermal energy, pulse energy, laser energy, ultrasound energy, microwave energy, and/or the like) to tissue to generate an opening at the target location in the patient.

According to some embodiments, the ablation mechanism 1204 is disposed on an outer member 1210 of the ablation shaft 1208, and the ablation mechanism 1204 and the ablation shaft 1208 are together slidable into and out of a lumen of a crimping shaft 1212. In certain embodiments, after the puncture element 1202 forms an opening in the tissue at a target location in a patient, the ablation mechanism 1204 expands to enlarge the opening in the tissue. In some embodiments, the ablation mechanism 1204 receives energy from an energy source and delivers ablation energy (such as radiofrequency (RF) energy, phased RF energy, cryogenic energy, thermal energy, pulse energy, laser energy, ultrasound energy, microwave energy, and/or the like) to ablate the tissue and thereby solidify the opening at the target location.

In some embodiments, the ablation mechanism 1204 includes an expandable cage 1214, and the expandable cage 1214 is fixedly coupled at its proximal end to the ablation shaft 1208 (for example, via reflow soldering or adhesives). In certain embodiments, the expandable cage 1214 includes a distal hub 1216 for coupling to the ablation shaft 1208. In other embodiments, the expandable cage 1214 lacks the distal hub 1216 and includes an open distal end (that is, being disposed apart from an ablation shaft). In certain embodiments, the expandable cage 1214 is made of one or more materials that facilitate self-expansion, such as nitinol, or one or more other materials, such as stainless steel, titanium, platinum-iridium, or cobalt-chromium.

In some embodiments, the expandable cage 1214 includes a plurality of expandable struts 1218. In certain embodiments and as illustrated, the expandable cage 1214 includes eight expandable struts 1218. In some embodiments, the expandable cage 1214 includes a different number of expandable struts 1218, such as two, three, four, five, six, seven, nine, ten, or more expandable struts 1218. In certain embodiments, each expandable strut 1218 includes a proximal loop 1220, a distal loop 1222, and a longitudinally extending portion 1224 coupling the loops 1220 and 1222. In other embodiments, the expandable struts 1218 have different structures.

In certain embodiments and as illustrated, the expandable cage 1214 carries an electrode structure 1226. In some embodiments, the electrode structure 1226 is configured to contact tissue at a target location in a patient and deliver ablation energy to the tissue. In certain embodiments, the electrode structure 1226 includes one or more electrodes. In some embodiments, the electrode structure 1226 includes a thin film electrode. In some embodiments, the electrode structure 1226 includes a thin film substrate and one or more electrodes are disposed on the thin film substrate. In certain embodiments, the one or more electrodes includes two or more electrodes. In some embodiments, at least two of the one or more electrodes form an electrode pair. In certain embodiments, the electrode structure 1226 has a length in a range of 4 mm to 12 mm. In certain embodiments, the electrode structure 1226 has an expanded diameter in a range of 2 mm to 10 mm. In certain embodiments, the ablation mechanism 1204 lacks the electrode structure 1226, and the expandable struts 1218 instead contact tissue at a target location within a patient and act as electrodes to deliver ablation energy to the tissue. In some embodiments, one or more portions of the expandable struts 1218 may carry an insulating coating (such as polyether ether ketone (PEEK), expanded polytetrafluoroethylene (ePTFE), elastomeric coatings, or the like) to inhibit delivery of ablation energy to the blood of the patient.

Figure 13:
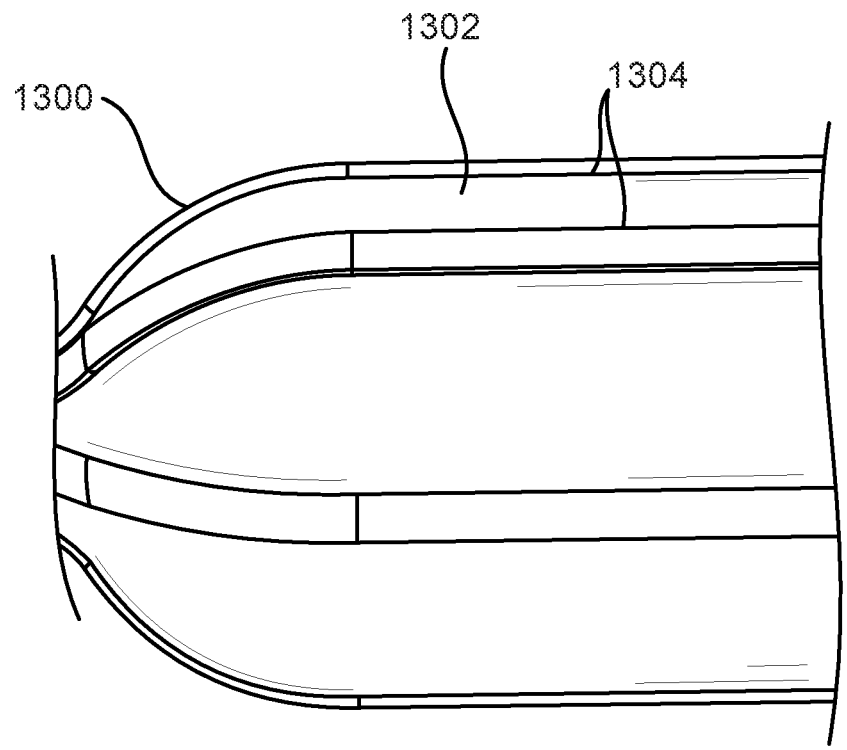
FIG. 13 is a schematic diagram of a side view of examples of an expandable cage and an actuator, in accordance with embodiments of the present disclosure.

FIG. 13 is a schematic diagram of a side view of examples of an expandable cage 1300 and an actuator 1302 of an ablation assembly, in accordance with embodiments of the present disclosure. In certain embodiments, the expandable cage 1300 carries one or more electrodes for receiving energy from an energy source and delivering ablation energy to tissue at a target location in a patient. In certain embodiments, the expandable cage 1300 contacts tissue at a target location in a patient and act as an electrode to deliver ablation energy to the tissue. In such embodiments, one or more portions of the expandable cage 1300 may carry an insulating coating (such as polyether ether ketone (PEEK), expanded polytetrafluoroethylene (ePTFE), elastomeric coatings, or the like) to inhibit delivery of ablation energy to the blood of the patient.

In certain embodiments, the expandable cage 1300 is made of one or more materials including as nitinol, stainless steel, titanium, platinum-iridium, or cobalt-chromium, or the like. In some embodiments, the expandable cage 1300 includes a plurality of expandable struts 1304. In certain embodiments, the expandable cage 1300 includes six expandable struts 1304. In other embodiments, the expandable cage 1300 includes a different number of expandable struts 1304, such as two, three, four, five, seven, eight, nine, ten, or more expandable struts 1304.

The actuator 1302 is disposed within the expandable cage 1300, and the actuator 1302 is configured to expand the expandable cage 1300. In certain embodiments and as illustrated, the actuator 1302 may be an inflatable balloon. Such a balloon may be made of one or more flexible and/or elastic materials, such as polyesters, polyamides, polyether block amides, polyethylene terephthalate, or the like. In other embodiments, the actuator 1302 takes different forms.

Figure 14:
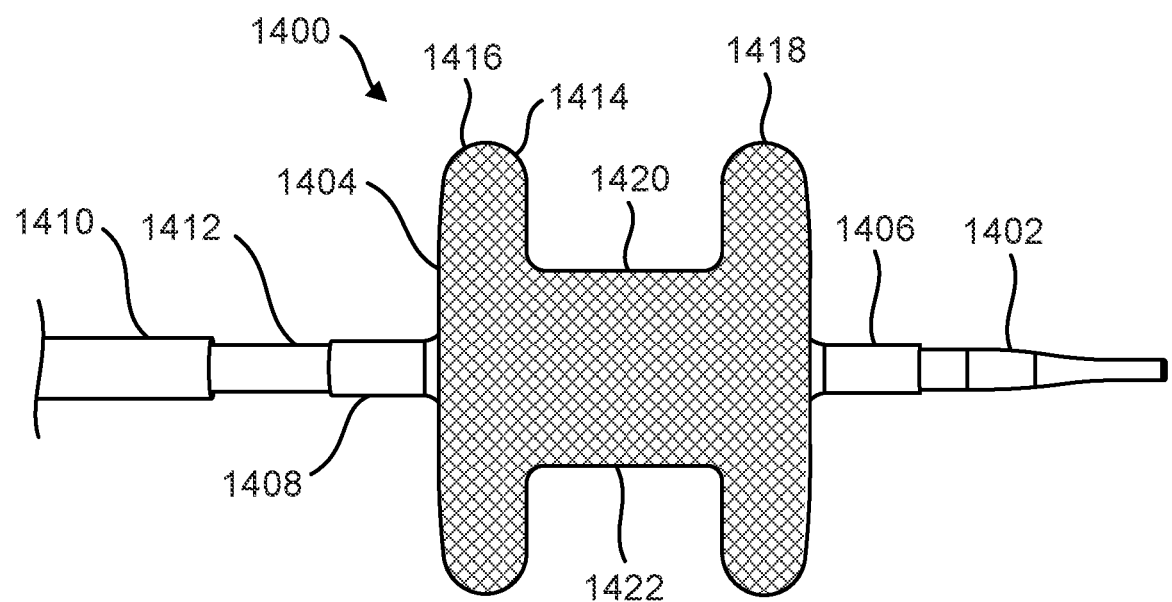
FIG. 14 is a schematic diagram of a side view of an example of an ablation assembly, in accordance with embodiments of the present disclosure.

FIG. 14 is a schematic diagram of a side view of an example of an expandable ablation assembly 1400 in an expanded state, in accordance with embodiments of the present disclosure. In certain embodiments, the ablation assembly 1400 includes an ablation shaft 1402 and an ablation mechanism 1404. In some embodiments, the ablation shaft 1402 may include a guidewire lumen (not shown) for receiving a guidewire and permitting the ablation assembly 1400 to track the guidewire to a target location in a patient, such as the AS of the patient or a vessel wall, more specifically the wall between the CS and LA of the patient. In some embodiments, the ablation shaft 1402 fixedly carries a distal end 1406 of the ablation mechanism 1404 and movably carries a proximal end 1408 of the ablation assembly 1400. In certain embodiments, the distal end of the ablation shaft 1402 includes a puncture element (not shown) for physically contacting tissue to puncture an opening at the target location in the patient and/or delivering ablation energy (such as radiofrequency (RF) energy, phased RF energy, cryogenic energy, thermal energy, pulse energy, laser energy, ultrasound energy, microwave energy, and/or the like) to tissue to puncture an opening at the target location in the patient.

According to some embodiments, after a guidewire forms an opening in the tissue at a target location in a patient, the ablation assembly 1400 is advanced along the guidewire such that the ablation mechanism 1404 is positioned in the opening. In certain embodiments, a crimping shaft 1410 is retracted from the ablation mechanism 1404, and the ablation mechanism 1404 expands (for example, with the retraction) to enlarge the opening in the tissue. In certain embodiments, the ablation mechanism 1404 is expanded by pushing an intermediate shaft 1412 relative to the ablation shaft 1402. In certain embodiments, the ablation mechanism 1404 is expanded via a different actuator, such as an inflatable balloon. In certain embodiments, the ablation mechanism 1404 self-expands. In some embodiments, the ablation mechanism 1404 then receives and delivers ablation energy (such as radiofrequency (RF) energy, phased RF energy, cryogenic energy, thermal energy, pulse energy, laser energy, ultrasound energy, microwave energy, and/or the like) to ablate the tissue and thereby solidify the opening at the target location.

According to certain embodiments, the ablation mechanism 1404 includes an expandable cage 1414. In certain embodiments, the expandable cage 1414 contacts tissue at a target location in a patient and acts as an electrode to deliver ablation energy to the tissue. In such embodiments, one or more portions of the expandable cage 1414 may carry an insulating coating (such as polyether ether ketone (PEEK), expanded polytetrafluoroethylene (ePTFE), elastomeric coatings, or the like) to inhibit delivery of ablation energy to the blood of the patient. As a more specific example, the expandable cage 1414 may have a spool-like shape, as illustrated, including a first coated end 1416, a second coated end 1418, and an intermediate uncoated portion 1420. In certain embodiments, the coated ends 1416, 1418 may be positioned outside of the opening at the target location in the patient, and the intermediate uncoated portion 1420 may be positioned in the opening at the target location in the patient. In some embodiments, the expandable cage 1414 carries one or more electrodes for delivering ablation energy to tissue at the target location in the patient.

In certain embodiments, the expandable cage 1414 is made of one or more shape-memory materials, such as nitinol, or one or more other materials, such as stainless steel, titanium, platinum-iridium, or cobalt-chromium. In some embodiments, the expandable cage 1414 includes a plurality of expandable struts, more specifically a plurality of braided wires 1422. In certain embodiments and as illustrated, the braided wires 1422 may generally include a first set of wires that extend helically in a first direction and a second set of wires that extend helically in a second, opposite direction. Alternatively, the braided wires 1422 may have different arrangements.

Figures 15A, 15B:
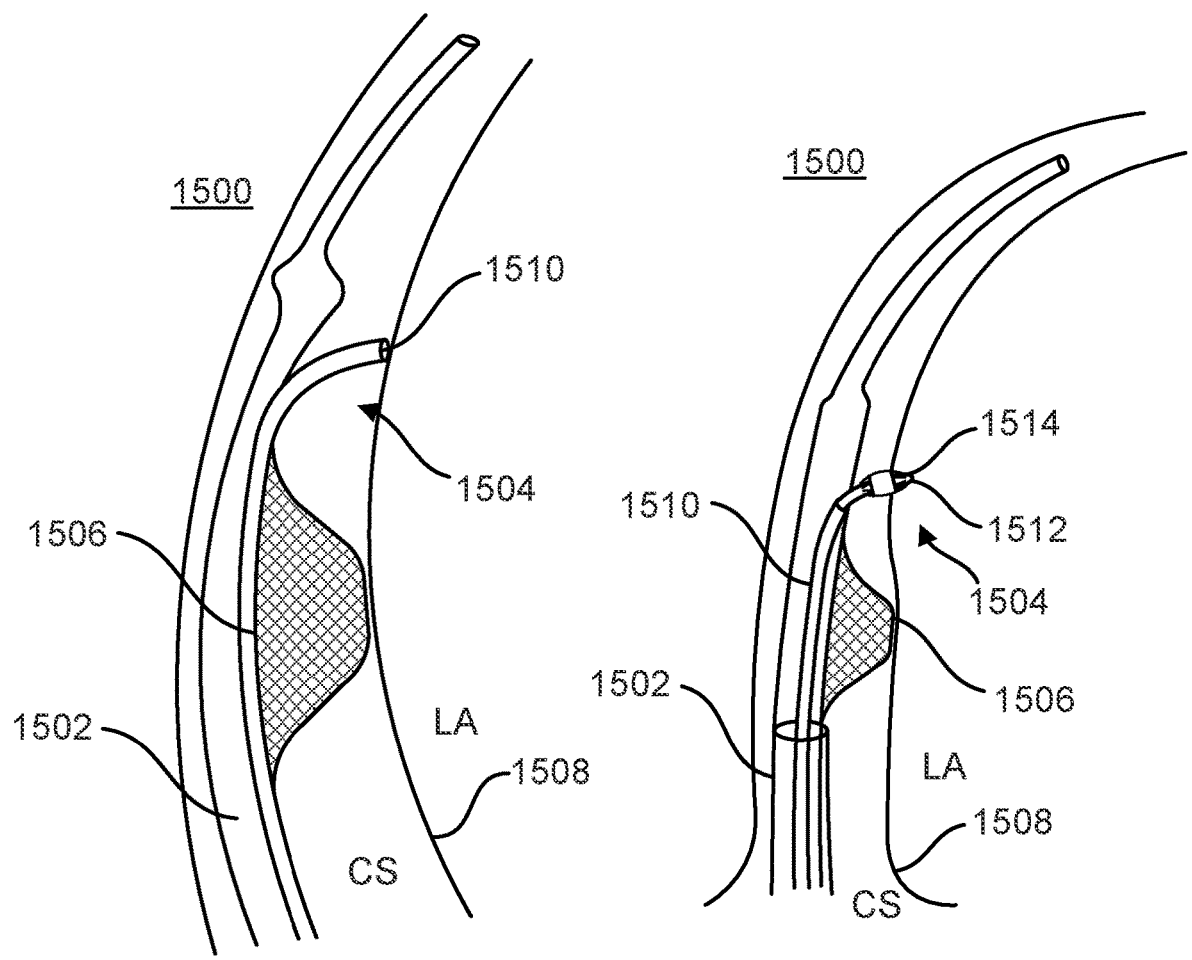
FIGS. 15A-15B are schematic diagrams of side views of an example of a shunting catheter, according to certain embodiments of the present disclosure.

FIGS. 15A-B are schematic diagrams of side views of an example of a shunting catheter 1500, according to certain embodiments of the present disclosure. FIGS. 15A-B are merely examples. One of the ordinary skilled in the art would recognize many variations, alternatives, and modifications. In some embodiments and as shown, the shunting catheter 1500 includes a catheter shaft 1502 and an ablation assembly 1504.

In some embodiments, the ablation assembly 1504 is disposed within the catheter shaft 1502 at a first state (for example, during deployment, during deployment to position the ablation assembly 1504). In some embodiments, the ablation assembly 1504 is extended from the catheter shaft 1502 at a second state (for example, during shunting).

According to certain embodiments, the shunting catheter 1500 includes an apposition element 1506 configured to be disposed within the catheter shaft 1502 at a first state (for example, during deployment), and protrudes from the catheter shaft 1502 at a second state (for example, during shunting). According to some embodiments, for example during the tracking of the shunting catheter 1500 to a target location in a patient's CS, the ablation assembly 1504 may be translated out of the catheter shaft 1502 to puncture a target location on a wall 1508 (for example, a vessel wall between a patient's CS and LA). In embodiments, the apposition element 1506 is made of a flexible material and configured to appose a vessel wall 1508 (for example, a vessel wall between a patient's CS and LA) during shunting. In some embodiments, the apposition element 1506 provides stability to the shunting catheter 1500 during deployment and/or shunting.

In some embodiments, the ablation assembly 1504 includes a crimping shaft 1510 having a predetermined curve, a puncture element 1512, and an ablation mechanism 1514. In some embodiments, the ablation assembly 1504 may have a telescoping feature (for example, the puncture element 1512 and the ablation mechanism 1514 are retractable into the crimping shaft 1510) to allow for the blunt end of the crimping shaft 1510 to contact the wall 1508 before the puncture element 1512 is translated forward to make contact with the wall 1508. In certain embodiments, the telescoping feature of the ablation assembly 1504 allows for a safe delivery of the puncture element 1512 to the target location.

In some embodiments, for example as shown in FIG. 15A, the ablation assembly 1504 has a first deployed state where the ablation assembly 1504 is extended from the catheter shaft 1502, and the puncture element 1512 and the ablation mechanism 1514 are retracted and crimped inside the crimping shaft 1510. In certain embodiments and as shown, the distal end of the ablation assembly 1504 is blunt during the first deployment state, such that if adjustment of position is needed, the wall surrounding the target location would only make contact with a blunt surface.

In some embodiments, for example as shown in FIG. 15B, the ablation assembly 1504 has a second deployed state where the ablation assembly 1504 is extended from the catheter shaft 1502, and the puncture element 1512 and the ablation mechanism 1514 are all protruded from the crimping shaft 1510. In certain embodiments, the puncture element 1512 punctures an opening in the wall 1508 in the patient upon moving from the first deployed state to the second deployed state. In certain embodiments, the ablation assembly 1504 is expanded in the second deployed state and thereby enlarges the opening in the wall 1508 in the patient. In certain embodiments, the ablation assembly 1504 ablates tissue at the opening in the wall 1508 in the patient by delivering ablation energy (such as radiofrequency (RF) energy, phased RF energy, cryogenic energy, thermal energy, pulse energy, laser energy, microwave energy, ultrasound energy, and/or the like) to the tissue.

Figure 16A:
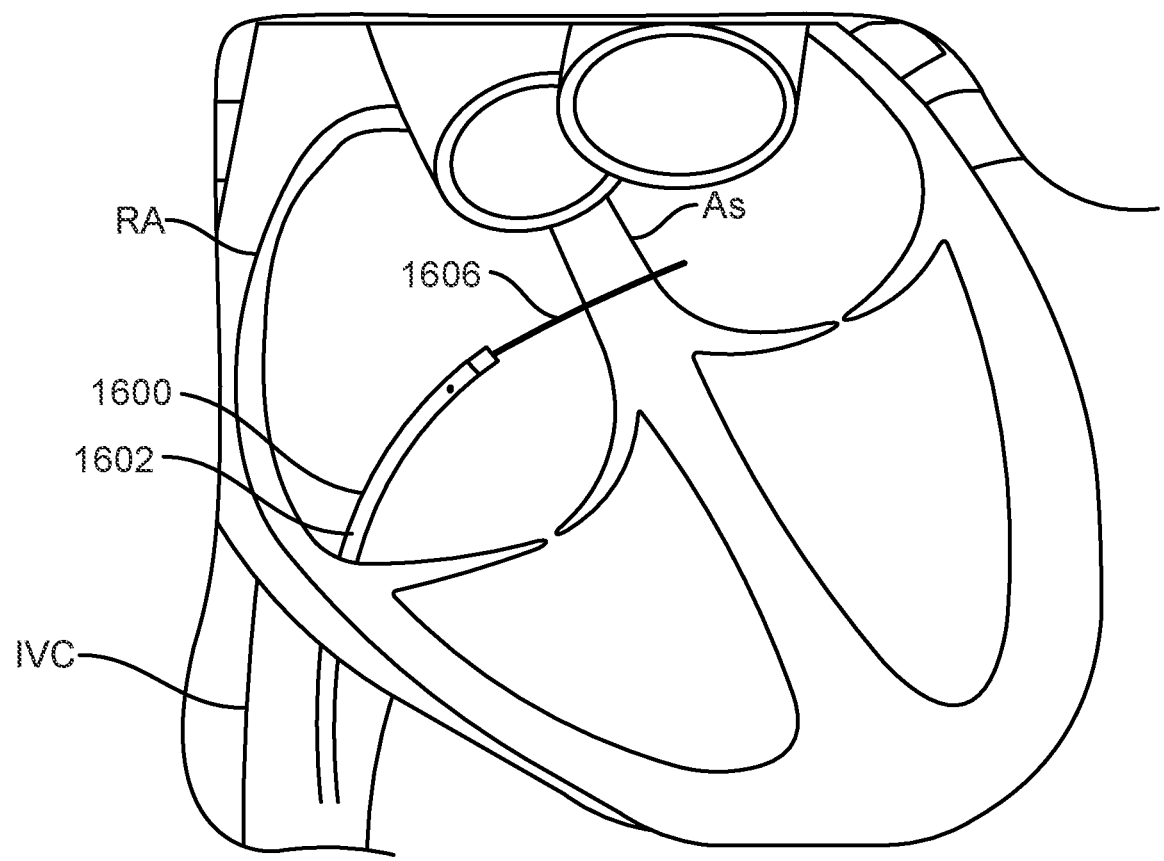
FIGS. 16A-16C are schematic diagrams of side views of another example of a shunting catheter, according to certain embodiments of the present disclosure
Figure 16B:
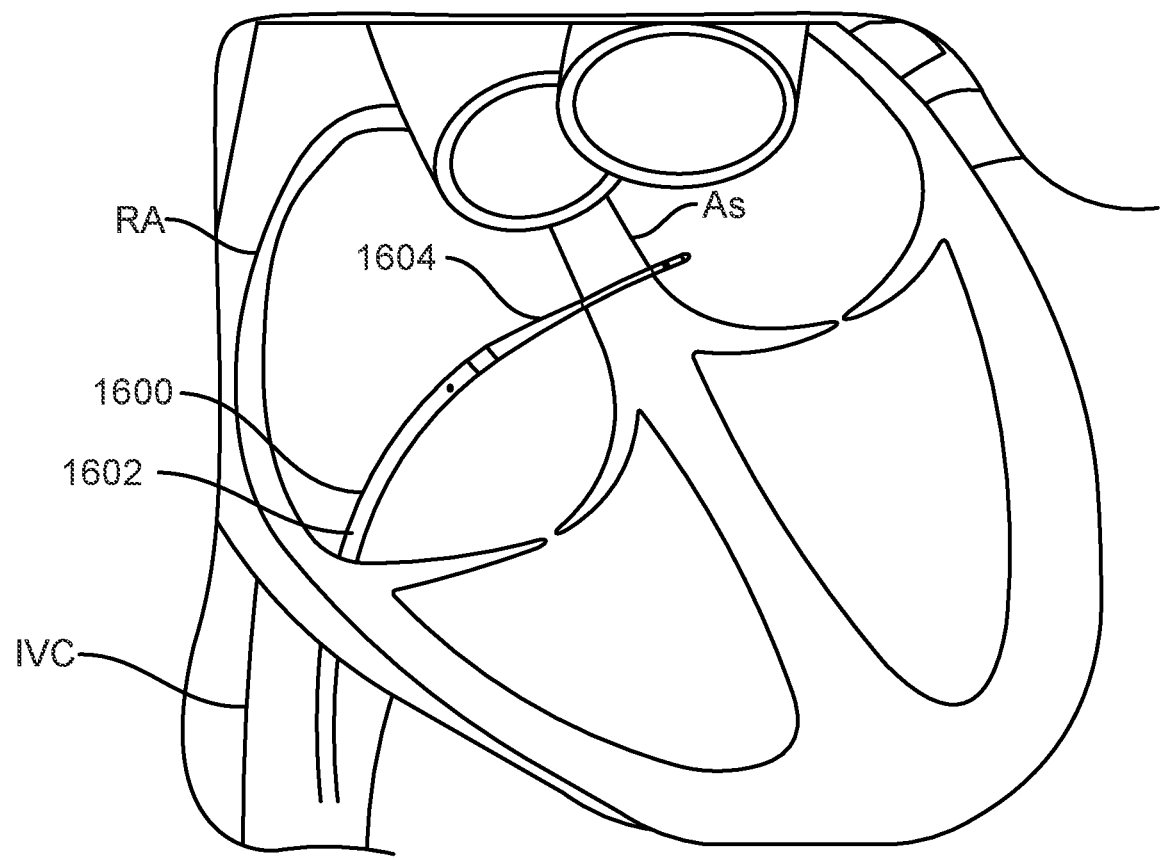
Figure 16C:
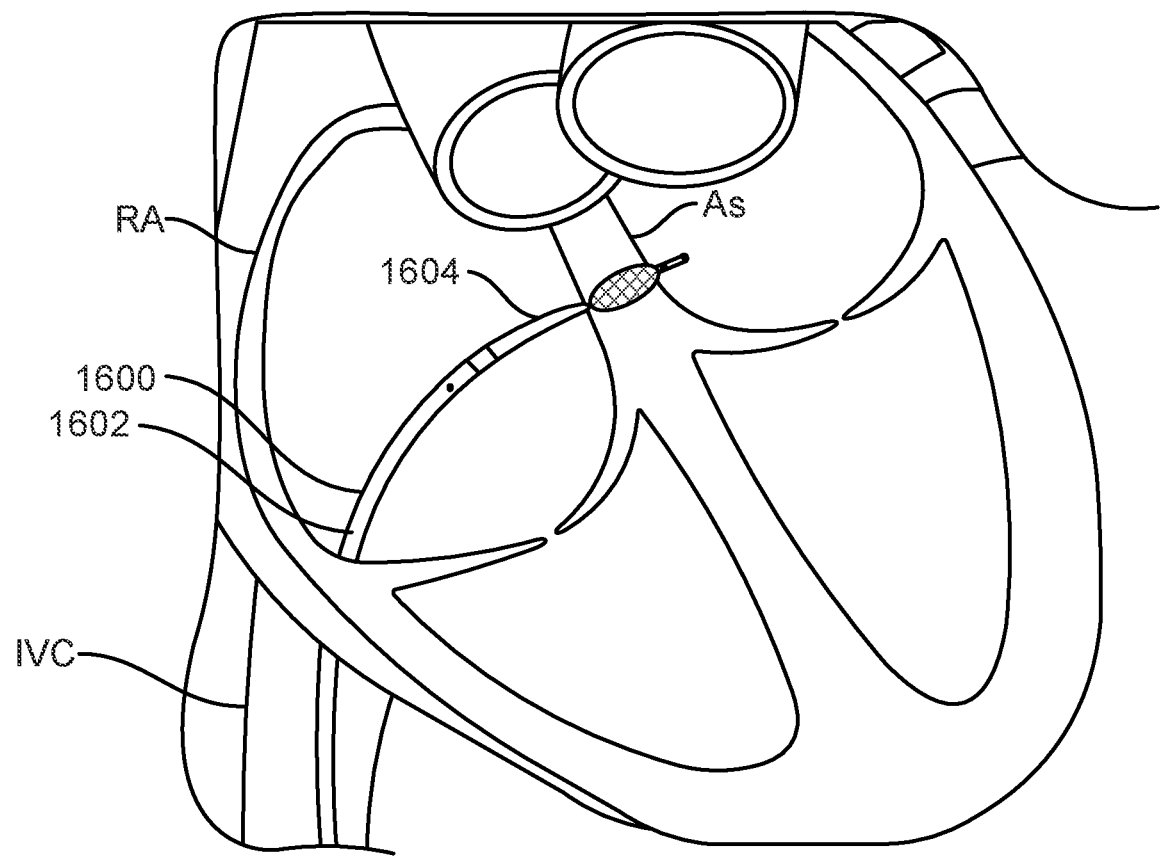

FIGS. 16A-C are schematic diagrams of side views of an example of a shunting catheter 1600, according to certain embodiments of the present disclosure. FIGS. 16A-C are merely examples. One of the ordinary skilled in the art would recognize many variations, alternatives, and modifications. In certain embodiments and as shown, the shunting catheter 1600 includes a catheter shaft 1602 and an ablation assembly 1604.

In some embodiments, the ablation assembly 1604 is disposed within the catheter shaft 1602 at a first state (for example, during deployment, during deployment to position the ablation assembly 1604). In some embodiments, the ablation assembly 1604 is extended from the catheter shaft 1602 at a second state (for example, during shunting). In certain embodiments, the ablation assembly 1604 is extended from an end of the catheter shaft 1602 at the second state.

According to certain embodiments and as shown in FIG. 16A, a guidewire 1606 is advanced through the vasculature (for example, the IVC and the RA) and punctures an opening in the tissue at a target location in a patient (for example, the patient's AS). According to some embodiments and as shown in FIG. 16B, for example after using the guidewire 1606 to advance the shunting catheter 1600 to the target location in a patient's AS, the ablation assembly 1604 has a first deployed state in which the ablation assembly 1604 is translated out of the catheter shaft 1602 and enters the opening formed at the target location. In certain embodiments and as shown in FIG. 16C, the ablation assembly 1604 has a second deployed state in which the ablation assembly 1604 is expanded and thereby enlarges the opening in the target location of the patient. In certain embodiments, the ablation assembly 1604 ablates tissue at the opening in the target location of the patient by delivering ablation energy (such as radiofrequency (RF) energy, phased RF energy, cryogenic energy, thermal energy, pulse energy, laser energy, microwave energy, ultrasound energy, and/or the like) to the tissue.

Figure 17:
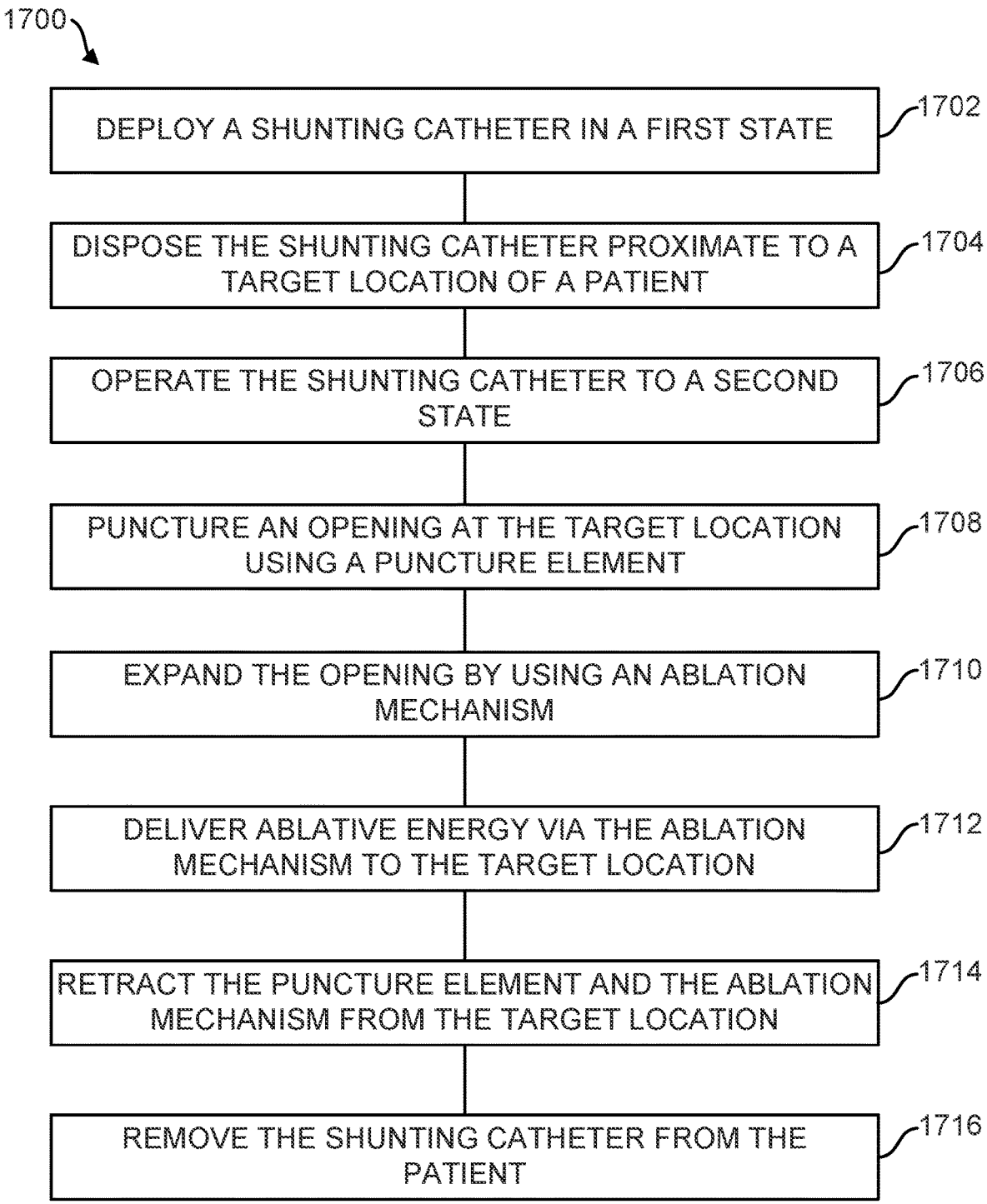
FIG. 17 is a flow diagram illustrating an example method of creating a shunt in a patient, in accordance with embodiments of the present disclosure.

FIG. 17 is a flow diagram illustrating an example method 1700 of creating a shunt in a patient, in accordance with embodiments of the present disclosure. Aspects of embodiments of the method may be performed, for example, by a shunting catheter system or a controller (for example, the system 104 in FIG. 1, the controller 112 in FIG. 1). One or more steps of method are optional and/or can be modified by one or more steps of other embodiments described herein. Additionally, one or more steps of other embodiments described herein may be added to the method. In some embodiments, the shunt may be formed in a coronary sinus of a patient. In certain embodiments, the shunt includes an opening between a patient's coronary sinus and left atrium.

At step 1702, the method 1700 includes deploying a shunting catheter in a first state, the shunting catheter including a catheter shaft including a shaft lumen and an ablation shaft disposed in the shaft lumen at the first state. In some embodiments, an ablation mechanism is disposed on the ablation shaft, and the ablation mechanism includes a plurality of expandable struts. In some embodiments, the ablation mechanism is configured to receive energy (for example, electrical energy) from an energy source. In certain embodiments, deploying the shunting catheter includes inserting the shunting catheter through a superior vena cava of a patient into a coronary sinus of the patient. In certain embodiments, deploying the shunting catheter includes inserting the shunting catheter through an inferior vena cava of a patient into a coronary sinus of the patient.

At step 1704, the method 1700 includes disposing the shunting catheter proximate to a target location of a patient. At step 1706, the method 1700 includes operating the shunting catheter to a second state (for example, a first deployed state, a second deployed state), wherein the ablation shaft is extended from the catheter shaft and the ablation mechanism is expandable. In certain embodiments, the ablation mechanism is disposed in the ablation shaft at the first deployed state. In some embodiments, the ablation shaft is extended from a side opening of the catheter shaft. In certain embodiments, the ablation shaft is extended from an end of the catheter shaft. In some embodiments, operating the shunting catheter to the second state further includes retracting a crimping shaft from a puncture element and the ablation mechanism of the shunting catheter. In some embodiments, the shunting catheter includes an apposition element disposed proximate to the ablation mechanism, and the apposition element is protruded from the catheter shaft at the second state.

At step 1708, the method 1700 includes puncturing, using the puncture element of the shunting catheter, an opening at the target location. In some embodiments, the target location is at a coronary sinus of a patient. In some embodiments, the puncture element physically contacts tissue to puncture an opening at the target location in the patient. Additionally or alternatively, the puncture element receives energy (for example, electrical energy) and delivers ablation energy (such as radiofrequency (RF) energy, phased RF energy, cryogenic energy, thermal energy, pulse energy, laser energy, ultrasound energy, microwave energy, and/or the like) to tissue to puncture an opening at the target location in the patient. In some instances, the method 1700 may include stabilizing the ablation mechanism in the second state, and before puncturing the opening at the target location.

At step 1710, the method 1700 includes expanding the opening using the ablation mechanism. In some embodiments, expanding the opening includes permitting the expandable struts to self-expand in the second state. In some embodiments, expanding the opening includes expanding the expandable struts by operating an actuator, for example inflating a balloon carried within the ablation mechanism.

At step 1712, the method 1700 includes delivering ablation energy (such as radiofrequency (RF) energy, phased RF energy, cryogenic energy, thermal energy, pulse energy, laser energy, ultrasound energy, microwave energy, and/or the like) via the ablation mechanism to tissue at the target location. In some embodiments, the ablation mechanism delivers the ablation energy while expanded in the second state. In some embodiments, delivering the ablation energy to the tissue at the target location solidifies the opening at the target location.

At step 1714, the method 1700 includes retracting the puncture element and the ablation mechanism from the tissue at the target location in the patient. In certain embodiments, retracting the puncture element and the ablation mechanism includes moving the puncture element and the ablation mechanism into the crimping shaft. In certain embodiments, retracting the puncture element and the ablation mechanism includes compressing the ablation mechanism in the crimping shaft.

At step 1716, the method 1700 includes removing the shunting catheter from a patient. In some embodiments, the method 1700 may include removing the shunting catheter, which includes removing the catheter shaft, the puncture element, and the ablation mechanism. In certain embodiments, the method 1700 does not leave any implant device at the target location. In some embodiments, the formed shunt is an opening between a coronary sinus and a left atrium of a patient. In certain embodiments, the shunting catheter is removed from the coronary sinus of the patient. In certain embodiments, the formed shunt is an opening that does not include an implant (for example, a frame or structure to support an opening). In some embodiments, the shunt includes an opening between the coronary sinus and the left atrium of a patient, where the shunt does not include an implant.

According to some embodiments, the method 1700 includes generating a shunt using a puncture element and an ablation mechanism of a shunting catheter. In certain embodiments, the shunt includes an expanded opening between the coronary sinus and left atrium of a patient. In some embodiments, the shunt does not include any implant.

Figure 18:
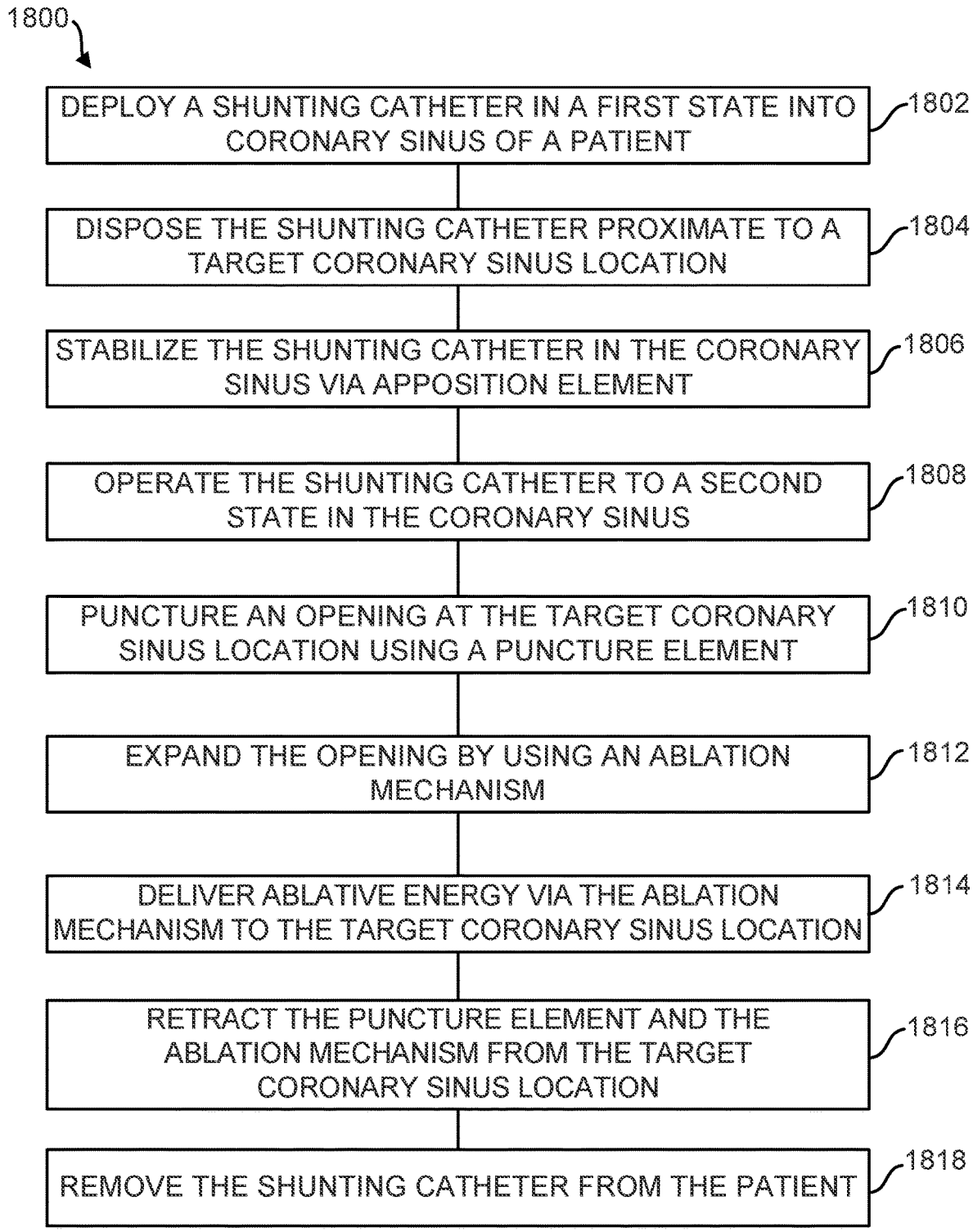
FIG. 18 is a flow diagram illustrating another example method of creating a shunt in a patient, in accordance with embodiments of the present disclosure.

FIG. 18 is a flow diagram illustrating an example method 1800 of creating a shunt in a patient, in accordance with embodiments of the present disclosure. Aspects of embodiments of the method may be performed, for example, by a shunting catheter system or a controller (for example, the system 104 in FIG. 1, the controller 112 in FIG. 1). One or more steps of method are optional and/or can be modified by one or more steps of other embodiments described herein. Additionally, one or more steps of other embodiments described herein may be added to the method.

At step 1802, the method 1800 includes deploying a shunting catheter in a first state into a coronary sinus of a patient, the shunting catheter including a catheter shaft including a shaft lumen and an ablation shaft disposed in the shaft lumen at the first state. In certain embodiments, an ablation mechanism is disposed on the ablation shaft, and the ablation mechanism includes a plurality of expandable struts. In some embodiments, the ablation mechanism is configured to receive energy from an energy source. In certain embodiments, the shunting catheter tracks along a guidewire to deploy into the coronary sinus of the patient. In certain embodiments, deploying the shunting catheter includes inserting the shunting catheter through a superior vena cava of a patient into a coronary sinus of the patient. In certain embodiments, deploying the shunting catheter includes inserting the shunting catheter through an inferior vena cava of a patient into a coronary sinus of the patient.

At step 1804, the method 1800 includes disposing the shunting catheter proximate to a target coronary sinus location of the patient. At step 1806, the method 1800 includes stabilizing the shunting catheter in the coronary sinus by protruding an apposition element from the catheter shaft and contact the wall of the coronary sinus. At step 1808, the method 1800 includes operating the shunting catheter to a second state, wherein a puncture element and the ablation mechanism are extended from the catheter shaft and the ablation mechanism is expandable. In some embodiments, operating the shunting catheter to the second state further includes retracting a crimping shaft from the puncture element and the ablation mechanism of the shunting catheter.

At step 1810, the method 1800 includes puncturing, using a puncture element of the shunting catheter, an opening at the target coronary sinus location. In some embodiments, the puncture element physically contacts tissue to puncture an opening at the target coronary sinus location. Additionally or alternatively, the puncture element delivers ablation energy (such as radiofrequency (RF) energy, phased RF energy, cryogenic energy, thermal energy, pulse energy, laser energy, ultrasound energy, microwave energy, and/or the like) to tissue to puncture an opening at the target coronary sinus location.

At step 1812, the method 1800 includes expanding the opening at the target coronary sinus location using the ablation mechanism. In some embodiments, expanding the opening includes permitting the ablation mechanism to self-expand in the second state. In some embodiments, expanding the opening includes expanding the ablation mechanism by operating an actuator, for example inflating a balloon carried within the ablation mechanism.

At step 1814, the method 1800 includes delivering ablation energy (such as radiofrequency (RF) energy, phased RF energy, cryogenic energy, thermal energy, pulse energy, laser energy, ultrasound energy, microwave energy, and/or the like) via the ablation mechanism to tissue at the target coronary sinus location. In some embodiments, the ablation mechanism delivers the ablation energy while expanded in the second state. In some embodiments, delivering the ablation energy to the tissue at the target coronary sinus location solidifies the opening at the target coronary sinus location.

At step 1816, the method 1800 includes retracting the puncture element and the ablation mechanism from the tissue at the target coronary sinus location. In certain embodiments, retracting the puncture element and the ablation mechanism includes moving the puncture element and the ablation mechanism into the crimping shaft. In certain embodiments, retracting the puncture element and the ablation mechanism includes compressing the ablation mechanism in the crimping shaft.

At step 1818, the method 1800 includes removing the shunting catheter from a patient. In some embodiments, the method 1800 may include removing the shunting catheter, which includes removing the catheter shaft, the puncture element, and the ablation mechanism. In certain embodiments, the method 1800 does not leave any implant device at the target coronary sinus location. In some embodiments, the formed shunt is an opening between the coronary sinus and the left atrium of a patient. In certain embodiments, the shunting catheter is removed from the coronary sinus of the patient. In certain embodiments, the formed shunt is an opening that does not include an implant (for example, a frame or structure to support an opening). In some embodiments, the shunt includes an opening between the coronary sinus and the left atrium of a patient, where the shunt does not include an implant.

According to some embodiments, the method 1800 includes generating a shunt using a puncture element and an ablation mechanism of a shunting catheter. In certain embodiments, the shunt includes an expanded opening between the coronary sinus and left atrium of a patient. In some embodiments, the shunt does not include any implant.

Figure 19:
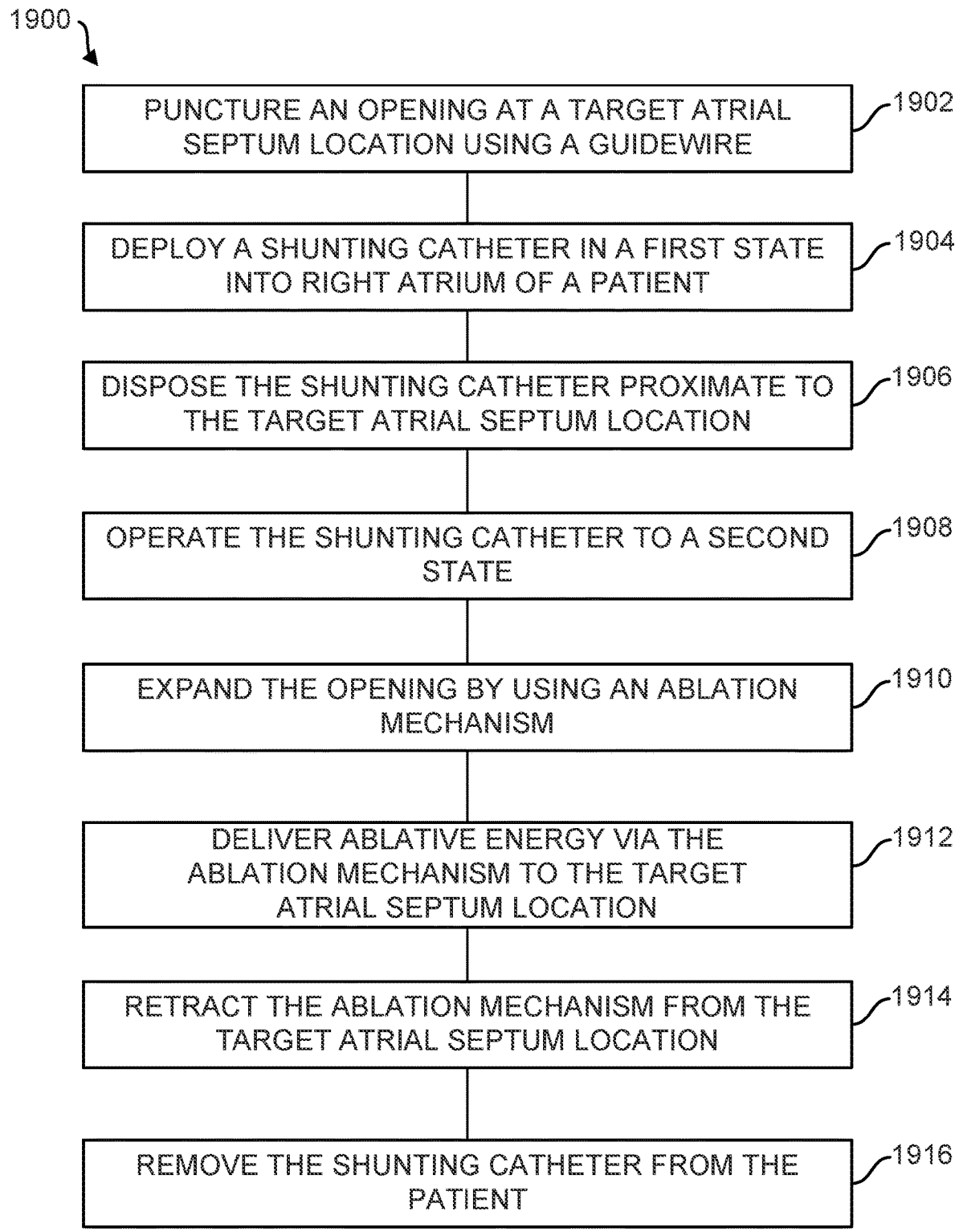
FIG. 19 is a flow diagram illustrating yet another example method of creating a shunt in a patient, in accordance with embodiments of the present disclosure.

FIG. 19 is a flow diagram illustrating an example method 1900 of creating a shunt in a patient, in accordance with embodiments of the present disclosure. Aspects of embodiments of the method may be performed, for example, by a shunting catheter system or a controller (for example, the ablation assembly 1400 in FIG. 14, the controller 112 in FIG. 1). One or more steps of method are optional and/or can be modified by one or more steps of other embodiments described herein. Additionally, one or more steps of other embodiments described herein may be added to the method.

At step 1902, the method 1900 includes puncturing, using a guidewire, an opening at a target atrial septum location in a patient. In some embodiments, the guidewire is inserted through an inferior vena cava of the patient into the RA of the patient to puncture the opening at the target atrial septum location. In some embodiments, the guidewire is inserted through a superior vena cava of the patient into the RA of the patient to puncture the opening at the target atrial septum location.

At step 1904, the method 1900 includes deploying a shunting catheter in a first state into a right atrium (RA) of a patient, the shunting catheter including a catheter shaft including a shaft lumen and an ablation shaft disposed in the shaft lumen at the first state. In certain embodiments, an ablation mechanism is disposed on the ablation shaft, and the ablation mechanism includes a plurality of expandable struts. In some embodiments, the ablation mechanism is configured to receive energy from an energy source. In certain embodiments, the shunting catheter tracks along the guidewire to deploy into the RA of the patient. In certain embodiments, deploying the shunting catheter includes inserting the shunting catheter through the inferior vena cava of the patient into the RA of the patient. In certain embodiments, deploying the shunting catheter includes inserting the shunting catheter through the superior vena cava of the patient into the RA of the patient.

At step 1906, the method 1900 includes disposing the shunting catheter proximate to a target atrial septum location of the patient. At step 1908, the method 1900 includes operating the shunting catheter to a second state, wherein the ablation mechanism is extended from the catheter shaft and the ablation mechanism is expandable. In some embodiments, operating the shunting catheter to the second state further includes positioning the ablation mechanism of the shunting catheter in the opening at the target atrial septum location. In some embodiments, operating the shunting catheter to the second state further includes retracting a crimping shaft from the ablation mechanism of the shunting catheter.

At step 1910, the method 1900 includes expanding the opening at the target atrial septum location using the ablation mechanism. In some embodiments, expanding the opening includes expanding the ablation mechanism by operating an actuator, for example pushing an intermediate shaft of the shunting catheter or inflating a balloon carried within the ablation mechanism. In some embodiments, expanding the opening includes permitting the ablation mechanism to self-expand in the second state.

At step 1912, the method 1900 includes delivering ablation energy (such as radiofrequency (RF) energy, phased RF energy, cryogenic energy, thermal energy, pulse energy, laser energy, ultrasound energy, microwave energy, and/or the like) via the ablation mechanism to tissue at the target atrial septum location. In some embodiments, the ablation mechanism delivers the ablation energy while expanded in the second state. In some embodiments, delivering the ablation energy to the tissue at the target atrial septum location solidifies the opening at the target atrial septum location.

At step 1914, the method 1900 includes retracting the ablation mechanism from the tissue at the target atrial septum location. In certain embodiments, retracting the ablation mechanism includes moving the ablation mechanism into the crimping shaft. In certain embodiments, retracting the ablation mechanism includes compressing the ablation mechanism in the crimping shaft.

At step 1918, the method 1900 includes removing the shunting catheter from the patient. In some embodiments, the method 1900 may include removing the shunting catheter, which includes removing the catheter shaft and the ablation mechanism. In certain embodiments, the method 1900 does not leave any implant device at the target coronary sinus location. In some embodiments, the formed shunt is an opening in the atrial septum of the patient. In certain embodiments, the shunting catheter is removed from the RA of the patient. In certain embodiments, the formed shunt is an opening that does not include an implant (for example, a frame or structure to support an opening). In some embodiments, the shunt includes an opening in the atrial septum of the patient, where the shunt does not include an implant.

According to some embodiments, the method 1900 includes generating a shunt using a guidewire and an ablation mechanism of a shunting catheter. In certain embodiments, the shunt includes an expanded opening in the atrial septum of the patient. In some embodiments, the shunt does not include any implant.

According to some embodiments, a shunting catheter includes: a catheter shaft including a shaft lumen; an ablation shaft disposed in the shaft lumen at a first state and extended from the catheter shaft at a second state; and an ablation mechanism disposed on the ablation shaft and expandable at the second state, the ablation mechanism including a plurality of expandable struts; wherein the ablation mechanism is configured to receive energy from an energy source and deliver ablation energy to a target location of a patient.

According to certain embodiments, the plurality of expandable struts are configured to act as electrodes and deliver the ablation energy to the target location of the patient.

According to some embodiments, the ablation mechanism further includes an electrode disposed on at least one of the plurality of expandable struts and configured to deliver the ablation energy to the target location of the patient.

According to certain embodiments, the electrode includes a base and a conductor carried by the base, the conductor configured to deliver the ablation energy to the target location of the patient.

According to some embodiments, the plurality of expandable struts include braided wires.

According to certain embodiments, the ablation mechanism includes a laser-cut tube, the laser-cut tube configured to be extended from the ablation shaft at the second state, wherein the plurality of expandable struts are disposed at an end of the laser-cut tube.

According to some embodiments, the plurality of expandable struts are self-expandable at the second state.

According to certain embodiments, further including an actuator being actuatable to expand the ablation mechanism.

According to some embodiments, the plurality of expandable struts include at least one selected from a group consisting of nitinol, stainless steel, titanium, platinum-iridium, and cobalt-chromium.

According to certain embodiments, further including a puncture element disposed proximate to a distal end of the ablation mechanism, the puncture element configured to puncture an opening at the target location of the patient.

According to some embodiments, further including a puncture element disposed proximate to a distal end of the ablation mechanism, the puncture element configured to deliver the ablation energy at an opening at the target location of the patient.

According to certain embodiments, the catheter shaft defines a first axis, the ablation shaft defines a second axis at the second state, and the second axis and the first axis form an angle greater than zero degrees.

According to some embodiments, a portion of the ablation mechanism includes an insulating coating configured to inhibit transmission of the ablation energy therethrough.

According to some embodiments, a method for creating a shunt includes: deploying a shunting catheter in a first state, the shunting catheter including: a catheter shaft including a shaft lumen; an ablation shaft disposed in the shaft lumen at a first state; and an ablation mechanism disposed on the ablation shaft and including a plurality of expandable struts; disposing the shunting catheter proximate to a target location of a patient; operating the shunting catheter to a second state, wherein the ablation shaft and the ablation mechanism extend from the catheter shaft; expanding an opening at the target location of the patient by expanding the plurality of expandable struts; and delivering ablation energy via the ablation mechanism to the target location of the patient.

According to certain embodiments, delivering the ablation energy includes delivering the ablation energy via the plurality of expandable struts to the target location of the patient.

According to some embodiments, the ablation mechanism further includes an electrode connected to the plurality of expandable struts, and wherein delivering the ablation energy includes delivering the ablation energy via the electrode to the target location of the patient.

According to certain embodiments, expanding the plurality of expandable struts includes permitting the plurality of expandable struts to self-expand.

According to some embodiments, permitting the plurality of expandable struts to self-expand includes retracting a crimping shaft from the plurality of expandable struts.

According to certain embodiments, the shunting catheter further includes an actuator, and wherein expanding the plurality of expandable struts includes actuating the actuator to expand the plurality of expandable struts.

According to some embodiments, expanding the plurality of expandable struts includes inflating a balloon to expand the plurality of expandable struts.

According to certain embodiments, the shunting catheter further includes a puncture element disposed proximate to a distal end of the ablation mechanism, and further including puncturing, using the puncture element, the opening at the target location before expanding the opening by expanding the plurality of expandable struts.

According to some embodiments, the shunting catheter further includes a puncture element disposed proximate to a distal end of the ablation mechanism, and further including forming the opening by delivering ablation energy to the target location of the patient via the puncture element before expanding the opening by expanding the plurality of expandable struts.

According to certain embodiments, the target location is at a coronary sinus of the patient.

According to some embodiments, the target location is at an atrial septum of the patient.

According to certain embodiments, a shunting catheter system includes: a shunting catheter, including: a catheter shaft including a shaft lumen; an ablation shaft disposed in the shaft lumen at a first state and extended from the catheter shaft at a second state; and an ablation mechanism disposed on the ablation shaft, the ablation mechanism including a plurality of expandable struts defining an expandable cage; an energy source connected to the shunting catheter; and a controller connected to the energy source and including a processor; wherein the processor is configured to control the energy source to deliver ablation energy to a target location of a patient via the ablation mechanism.

According to certain embodiments, the ablation energy includes at least one of radiofrequency (RF) energy, phased RF energy, cryogenic energy, thermal energy, pulse energy, laser energy, ultrasound energy, microwave energy.

According to some embodiments, the plurality of expandable struts act as electrodes and are configured to deliver the ablation energy to the target location of the patient.

According to certain embodiments, the ablation mechanism further includes an electrode connected to the expandable cage and configured to deliver the ablation energy to the target location of the patient.

According to some embodiments, the plurality of expandable struts include braided wires.

According to certain embodiments, the ablation mechanism includes a laser-cut tube, the laser-cut tube configured to be extended from the ablation shaft at the second state, wherein the plurality of expandable struts are disposed at an end of the laser-cut tube.

According to some embodiments, the plurality of expandable struts are self-expandable at the second state.

According to certain embodiments, the shunting catheter further includes an actuator being actuatable to expand the expandable cage.

According to some embodiments, further including a balloon configured to expand the expandable cage at the second state.

Various modifications and additions can be made to the exemplary embodiments discussed without departing from the scope of the present disclosure. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A shunting catheter, comprising:
a catheter shaft including a shaft lumen;
an ablation shaft disposed in the shaft lumen at a first state and extended from the catheter shaft at a second state; and
an ablation mechanism disposed on the ablation shaft and expandable at the second state, the ablation mechanism comprising a plurality of expandable struts;
wherein the ablation mechanism is configured to receive energy from an energy source and deliver ablation energy to a target location of a patient;
wherein the catheter shaft defines a first axis, the ablation shaft defines a second axis at the second state, and the second axis and the first axis form an angle greater than zero degrees.

2. The shunting catheter of claim 1, wherein the plurality of expandable struts are configured to act as electrodes and deliver the ablation energy to the target location of the patient.

3. The shunting catheter of claim 1, wherein the ablation mechanism further comprises an electrode disposed on at least one of the plurality of expandable struts and configured to deliver the ablation energy to the target location of the patient.

4. The shunting catheter of claim 1, wherein the plurality of expandable struts comprise braided wires.

5. The shunting catheter of claim 1, wherein the ablation mechanism comprises a laser-cut tube, the laser-cut tube configured to be extended from the ablation shaft at the second state, wherein the plurality of expandable struts are disposed at an end of the laser-cut tube.

6. The shunting catheter of claim 1, wherein the plurality of expandable struts are self-expandable at the second state.

7. The shunting catheter of claim 1, further comprising an actuator being actuatable to expand the ablation mechanism.

8. The shunting catheter of claim 1, wherein the plurality of expandable struts comprise at least one selected from a group consisting of nitinol, stainless steel, titanium, platinum-iridium, and cobalt-chromium.

9. The shunting catheter of claim 1, further comprising a puncture element disposed proximate to a distal end of the ablation mechanism, the puncture element configured to puncture an opening at the target location of the patient.

10. The shunting catheter of claim 1, further comprising a puncture element disposed proximate to a distal end of the ablation mechanism, the puncture element configured to deliver the ablation energy at an opening at the target location of the patient.

11. The shunting catheter of claim 1, wherein a portion of the ablation mechanism comprises an insulating coating configured to inhibit transmission of the ablation energy therethrough.

12. A method for creating a shunt, comprising:
deploying a shunting catheter in a first state, the shunting catheter comprising:
a catheter shaft including a shaft lumen, the catheter shaft defining a first axis;
an ablation shaft disposed in the shaft lumen at the first state;
an ablation mechanism disposed on the ablation shaft and comprising a plurality of expandable struts;
disposing the shunting catheter proximate to a target location of a patient;
operating the shunting catheter to a second state, wherein the ablation shaft and the ablation mechanism extend from the catheter shaft and the ablation shaft defines a second axis at the second state, and the second axis and the first axis form an angle greater than zero degrees;
expanding an opening at the target location of the patient by expanding the plurality of expandable struts; and
delivering ablation energy via the ablation mechanism to the target location of the patient.

13. The method of claim 12, wherein delivering the ablation energy comprises delivering the ablation energy via the plurality of expandable struts to the target location of the patient.

14. The method of claim 12, wherein the ablation mechanism further comprises an electrode connected to the plurality of expandable struts, and wherein delivering the ablation energy comprises delivering the ablation energy via the electrode to the target location of the patient.

15. The method of claim 12, wherein expanding the plurality of expandable struts comprises permitting the plurality of expandable struts to self-expand.

16. The method of claim 15, wherein permitting the plurality of expandable struts to self-expand comprises retracting a crimping shaft from the plurality of expandable struts.

17. The method of claim 12, wherein the shunting catheter further comprises an actuator, and wherein expanding the plurality of expandable struts comprises actuating the actuator to expand the plurality of expandable struts.

18. The method of claim 12, wherein the shunting catheter further comprises a puncture element disposed proximate to a distal end of the ablation mechanism, and further comprising puncturing, using the puncture element, the opening at the target location before expanding the opening by expanding the plurality of expandable struts.

19. The method of claim 12, wherein the shunting catheter further comprises a puncture element disposed proximate to a distal end of the ablation mechanism, and further comprising forming the opening by delivering ablation energy to the target location of the patient via the puncture element before expanding the opening by expanding the plurality of expandable struts.

20. The method of claim 12, wherein the target location is at a coronary sinus of the patient.

21. The method of claim 12, wherein the target location is at an atrial septum of the patient.

22. A shunting catheter system, comprising:
a shunting catheter, comprising:
   a catheter shaft including a shaft lumen;
   an ablation shaft disposed in the shaft lumen at a first state and extended from the catheter shaft at a second state;
   an ablation mechanism disposed on the ablation shaft, the ablation mechanism comprising a plurality of expandable struts defining an expandable cage;
an energy source connected to the shunting catheter; and
a controller connected to the energy source and comprising a processor;
wherein the processor is configured to control the energy source to deliver ablation energy to a target location of a patient via the ablation mechanism;
wherein the catheter shaft defines a first axis, the ablation shaft defines a second axis at the second state, and the second axis and the first axis form an angle greater than zero degrees.

23. The shunting catheter system of claim 22, wherein the ablation energy comprises at least one of radiofrequency (RF) energy, phased RF energy, cryogenic energy, thermal energy, pulse energy, laser energy, ultrasound energy, microwave energy.

24. The shunting catheter system of claim 22, wherein the plurality of expandable struts act as electrodes and are configured to deliver the ablation energy to the target location of the patient.

25. The shunting catheter system of claim 22, wherein the ablation mechanism further comprises an electrode connected to the expandable cage and configured to deliver the ablation energy to the target location of the patient.

26. The shunting catheter system of claim 22, wherein the ablation mechanism comprises a laser-cut tube, the laser-cut tube configured to be extended from the ablation shaft at the second state, wherein the plurality of expandable struts are disposed at an end of the laser-cut tube.

27. The shunting catheter system of claim 22, wherein the plurality of expandable struts are self-expandable at the second state.

28. The shunting catheter system of claim 22, wherein the shunting catheter further comprises an actuator being actuatable to expand the expandable cage.

29. A shunting catheter, comprising:
   a catheter shaft including a shaft lumen, the catheter shaft defining a first axis;
   an ablation shaft disposed in the shaft lumen at a first state and extended from the catheter shaft at a second state, the ablation shaft defines a second axis at the second state, and the second axis and the first axis form an angle greater than zero degrees; and
   an ablation mechanism disposed on the ablation shaft and expandable at the second state, the ablation mechanism comprising a plurality of expandable struts;
   wherein the ablation mechanism is configured to receive energy from an energy source and deliver ablation energy to a target location of a patient;
   wherein the ablation mechanism further comprises an electrode disposed on at least one of the plurality of expandable struts and configured to deliver the ablation energy to the target location of the patient;
   wherein the plurality of expandable struts are self-expandable at the second state.

* * * * *